(12) United States Patent
Jimenez et al.

(10) Patent No.: US 11,234,835 B2
(45) Date of Patent: Feb. 1, 2022

(54) TRANSVERSELY EXPANDABLE MINIMALLY INVASIVE INTERVERTEBRAL CAGE

(71) Applicant: Octagon Spine LLC, Seattle, WA (US)

(72) Inventors: Omar F. Jimenez, Seattle, WA (US); Yefim I. Safris, Golden Valley, MN (US)

(73) Assignee: Octagon Spine LLC, Seattle, WA (US)

( * ) Notice: Subject to any disclaimer, the term of this patent is extended or adjusted under 35 U.S.C. 154(b) by 136 days.

(21) Appl. No.: 16/292,565

(22) Filed: Mar. 5, 2019

(65) Prior Publication Data

US 2020/0281739 A1 Sep. 10, 2020

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/30014* (2013.01); *A61F 2002/30146* (2013.01); *A61F 2002/30405* (2013.01); *A61F 2002/30556* (2013.01); *A61F 2002/30579* (2013.01); *A61F 2002/30593* (2013.01); *A61F 2002/30622* (2013.01); *A61F 2002/4627* (2013.01); *A61F 2002/4635* (2013.01)

(58) Field of Classification Search
CPC ...... A61F 2/4455; A61F 2/446; A61F 2/4465; A61F 2/447; A61F 2002/30146; A61F 2002/30579
See application file for complete search history.

(56) References Cited

U.S. PATENT DOCUMENTS

| | | |
|---|---|---|
| 283,218 A | 8/1883 | Rycke |
| 703,251 A | 6/1902 | Haire |
| 811,344 A | 1/1906 | Wands |
| 1,388,836 A | 8/1921 | Ripsch et al. |

(Continued)

FOREIGN PATENT DOCUMENTS

| | | |
|---|---|---|
| EP | 1342456 A1 | 9/2003 |
| EP | 1552797 A2 | 7/2005 |

(Continued)

OTHER PUBLICATIONS

PCT/US2010/042941, filed Jul. 22, 2010, International Search Report and Written Opinion, dated Apr. 25, 2011.

(Continued)

*Primary Examiner* — Julianna N Harvey
(74) *Attorney, Agent, or Firm* — Patterson Thuente Pedersen, P.A.

(57) ABSTRACT

Disclosed herein are systems and methods for intervertebral body fusion that provide more robust support within the disc space. Intervertebral body fusion devices can have a unitary monolithic body including a plurality of body segments interconnected with each other by flexure members. Devices be configured to be inserted through an opening in a compressed configuration and then expanded within the disc space to an expanded configuration. In the expanded configuration, devices can have a greater mediolateral or transverse to the disc space footprint. This wider footprint provides greater support for the vertebrae relative to the size of the opening through which the device is inserted.

16 Claims, 23 Drawing Sheets

(56) References Cited

U.S. PATENT DOCUMENTS

| | | |
|---|---|---|
| 1,500,859 A | 7/1924 | Wright |
| 1,547,946 A | 7/1925 | Myers |
| 2,106,088 A | 1/1938 | De Tar |
| 2,231,221 A | 2/1941 | Rector |
| 2,453,656 A | 11/1948 | Bullard, III |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,109 A | 10/1984 | Kobelt |
| 4,516,303 A | 5/1985 | Kloster |
| 4,528,864 A | 7/1985 | Craig |
| 4,559,717 A | 12/1985 | Scire et al. |
| 4,630,495 A | 12/1986 | Smith |
| 4,691,586 A | 9/1987 | van Leijenhorst et al. |
| 4,694,703 A | 9/1987 | Routson |
| 4,869,552 A | 9/1989 | Tolleson et al. |
| 5,133,108 A | 7/1992 | Esnault |
| 5,172,442 A | 12/1992 | Bartley et al. |
| 5,181,371 A | 1/1993 | Deworth |
| 5,196,857 A | 3/1993 | Chiappetta et al. |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett et al. |
| 5,439,377 A | 8/1995 | Milanovich |
| 5,445,471 A | 8/1995 | Wexler et al. |
| 5,554,191 A | 9/1996 | Lahille et al. |
| 5,645,599 A | 7/1997 | Samani |
| 5,653,763 A | 8/1997 | Errico et al. |
| 5,664,457 A | 9/1997 | Nejati |
| 5,904,479 A | 5/1999 | Staples |
| 5,960,670 A | 10/1999 | Iverson et al. |
| 5,980,252 A | 11/1999 | Samchukov et al. |
| 5,988,006 A | 11/1999 | Fleytman |
| 6,039,761 A | 3/2000 | Li et al. |
| 6,045,579 A | 4/2000 | Hochshuler et al. |
| 6,056,491 A | 5/2000 | Hsu |
| 6,080,193 A | 6/2000 | Hochshuler et al. |
| 6,136,031 A | 10/2000 | Middleton |
| 6,175,989 B1 | 1/2001 | Carpentar et al. |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,454,807 B1 | 9/2002 | Jackson |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley et al. |
| 6,802,229 B1 | 10/2004 | Lambert |
| 6,808,537 B2 | 10/2004 | Michelson |
| 6,863,673 B2 | 3/2005 | Gerbec et al. |
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici et al. |
| 7,070,598 B2 | 7/2006 | Lim et al. |
| 7,087,055 B2 | 8/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith et al. |
| 7,316,381 B2 | 1/2008 | Häcker et al. |
| 7,410,201 B1 | 8/2008 | Wilson et al. |
| 7,425,103 B2 | 9/2008 | Perez-Sanchez |
| 7,431,735 B2 | 10/2008 | Liu et al. |
| 7,435,032 B1 | 10/2008 | Murphey et al. |
| 7,547,325 B2 | 6/2009 | Biedermann et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Trieu |
| 7,708,779 B2 | 5/2010 | Edie et al. |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,901,409 B2 | 3/2011 | Canaveral et al. |
| 7,947,078 B2 | 5/2011 | Siegal |
| 7,951,199 B2 | 5/2011 | Miller |
| 7,985,256 B2 | 7/2011 | Grotz et al. |
| 8,057,549 B2 | 11/2011 | Butterman et al. |
| 8,070,813 B2 | 12/2011 | Grotz et al. |
| 8,088,163 B1 | 1/2012 | Kleiner |
| 8,192,495 B2 | 6/2012 | Simpson et al. |
| 8,303,663 B2 | 11/2012 | Jimenez et al. |
| 8,496,706 B2 | 7/2013 | Ragab et al. |
| 8,523,944 B2 | 9/2013 | Jimenez et al. |
| 8,540,452 B2 | 9/2013 | Jimenez et al. |
| 8,628,577 B1 | 1/2014 | Jimenez |
| 8,636,746 B2 | 1/2014 | Jimenez et al. |
| 8,771,360 B2 | 7/2014 | Jimenez et al. |
| 8,795,366 B2 | 8/2014 | Varela |
| 8,894,712 B2 | 11/2014 | Varela |
| 8,906,100 B2 | 12/2014 | Jimenez |
| 8,932,302 B2 | 1/2015 | Jimenez et al. |
| 8,940,049 B1 | 1/2015 | Jimenez et al. |
| 9,358,125 B2 | 6/2016 | Jimenez et al. |
| 9,381,092 B2 | 7/2016 | Jimenez et al. |
| 9,445,917 B2 | 9/2016 | Jimenez et al. |
| 9,474,626 B2 | 10/2016 | Jimenez |
| 9,486,328 B2 | 11/2016 | Jimenez |
| 9,498,270 B2 | 11/2016 | Jimenez |
| 9,668,879 B2 | 6/2017 | Jimenez et al. |
| 9,867,717 B2 | 1/2018 | Jimenez |
| 10,060,469 B2 | 8/2018 | Jimenez et al. |
| 2002/0128716 A1 | 9/2002 | Cohen et al. |
| 2002/0138146 A1 | 9/2002 | Jackson |
| 2003/0077110 A1 | 4/2003 | Knowles |
| 2003/0233145 A1 | 12/2003 | Landry et al. |
| 2004/0049271 A1 | 3/2004 | Biedermann et al. |
| 2004/0111157 A1 | 6/2004 | Ralph et al. |
| 2004/0153156 A1 | 8/2004 | Cohen et al. |
| 2004/0193158 A1 | 9/2004 | Lim |
| 2004/0225364 A1 | 11/2004 | Richelsoph et al. |
| 2005/0000228 A1 | 1/2005 | De Sousa et al. |
| 2005/0033431 A1 | 2/2005 | Gordon et al. |
| 2005/0095384 A1 | 5/2005 | Wittmeyer, Jr. |
| 2005/0113921 A1 | 5/2005 | An et al. |
| 2005/0113924 A1 | 5/2005 | Buttermann |
| 2005/0175406 A1 | 8/2005 | Perez-Sanchez |
| 2005/0182416 A1 | 8/2005 | Lim et al. |
| 2005/0261769 A1 | 11/2005 | Moskowitz et al. |
| 2006/0004447 A1 | 1/2006 | Mastrorio et al. |
| 2006/0004455 A1 | 1/2006 | Leonard et al. |
| 2006/0025862 A1 | 2/2006 | Villiers et al. |
| 2006/0058878 A1 | 3/2006 | Michelson |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0253201 A1 | 11/2006 | McLuen |

(56) References Cited

U.S. PATENT DOCUMENTS

| | | |
|---|---|---|
| 2006/0293752 A1 | 12/2006 | Mounmene et al. |
| 2007/0032791 A1 | 2/2007 | Greenhalgh et al. |
| 2007/0049943 A1 | 3/2007 | Moskowitz et al. |
| 2007/0083267 A1 | 4/2007 | Miz et al. |
| 2007/0093901 A1 | 4/2007 | Grotz et al. |
| 2007/0129730 A1 | 6/2007 | Woods et al. |
| 2007/0173826 A1 | 7/2007 | Canaveral |
| 2007/0185577 A1 | 8/2007 | Malek |
| 2007/0191954 A1 | 8/2007 | Hansell et al. |
| 2007/0191958 A1 | 8/2007 | Abdou |
| 2007/0198089 A1 | 8/2007 | Moskowitz et al. |
| 2007/0219634 A1 | 9/2007 | Greenhalgh et al. |
| 2007/0222100 A1 | 9/2007 | Husted et al. |
| 2007/0250171 A1 | 10/2007 | Bonin, Jr. |
| 2007/0255415 A1 | 11/2007 | Edie et al. |
| 2007/0282449 A1 | 12/2007 | de Villiers et al. |
| 2007/0288092 A1 | 12/2007 | Bambakidis |
| 2007/0293329 A1 | 12/2007 | Glimpel et al. |
| 2007/0293948 A1 | 12/2007 | Bagga et al. |
| 2008/0026903 A1 | 1/2008 | Flugrad et al. |
| 2008/0077246 A1 | 3/2008 | Fehling et al. |
| 2008/0091211 A1 | 4/2008 | Gately |
| 2008/0100179 A1 | 5/2008 | Ruggeri et al. |
| 2008/0103601 A1 | 5/2008 | Biro et al. |
| 2008/0114367 A1 | 5/2008 | Meyer |
| 2008/0140207 A1 | 6/2008 | Olmos |
| 2008/0147194 A1 | 6/2008 | Grotz et al. |
| 2008/0154266 A1 | 6/2008 | Protopsaltis et al. |
| 2008/0161920 A1 | 7/2008 | Melkent |
| 2008/0161931 A1 | 7/2008 | Perez-Cruet et al. |
| 2008/0168855 A1 | 7/2008 | Giefer et al. |
| 2008/0183204 A1 | 7/2008 | Greenhalgh et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu et al. |
| 2008/0243255 A1* | 10/2008 | Butler ............ A61F 2/4465 623/17.16 |
| 2008/0281423 A1 | 11/2008 | Sheffer et al. |
| 2008/0292392 A1 | 11/2008 | Voellmer |
| 2008/0319487 A1 | 12/2008 | Fielding et al. |
| 2009/0012564 A1 | 1/2009 | Chirico et al. |
| 2009/0076614 A1 | 3/2009 | Arramon |
| 2009/0099568 A1 | 4/2009 | Lowry et al. |
| 2009/0164017 A1 | 6/2009 | Sommerich et al. |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0259316 A1 | 10/2009 | Ginn et al. |
| 2009/0299478 A1 | 12/2009 | Carls et al. |
| 2009/0306672 A1 | 12/2009 | Reindel et al. |
| 2010/0004688 A1 | 1/2010 | Maas et al. |
| 2010/0076557 A1 | 3/2010 | Miller |
| 2010/0082109 A1 | 4/2010 | Greenhalgh et al. |
| 2010/0094305 A1 | 4/2010 | Chang et al. |
| 2010/0161062 A1 | 6/2010 | Foley et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez et al. |
| 2011/0015638 A1 | 1/2011 | Pischl et al. |
| 2011/0054616 A1 | 3/2011 | Kamran et al. |
| 2011/0093075 A1 | 4/2011 | Duplessis et al. |
| 2011/0112644 A1 | 5/2011 | Zilberstein et al. |
| 2011/0138948 A1 | 6/2011 | Jimenez et al. |
| 2011/0160861 A1 | 6/2011 | Jimenez et al. |
| 2011/0172774 A1 | 7/2011 | Varela |
| 2011/0270398 A1 | 11/2011 | Grotz et al. |
| 2012/0010653 A1 | 1/2012 | Seifert et al. |
| 2012/0029636 A1 | 2/2012 | Ragab et al. |
| 2012/0083887 A1* | 4/2012 | Purcell ............ A61F 2/4611 623/17.16 |
| 2012/0116518 A1 | 5/2012 | Grotz et al. |
| 2012/0158071 A1 | 6/2012 | Jimenez et al. |
| 2012/0185049 A1 | 7/2012 | Varela |
| 2012/0226357 A1 | 9/2012 | Varela |
| 2012/0271419 A1 | 10/2012 | Marik |
| 2012/0290094 A1 | 11/2012 | Lim et al. |
| 2012/0303124 A1 | 11/2012 | McLuen et al. |
| 2012/0323329 A1 | 12/2012 | Jimenez et al. |
| 2013/0053966 A1 | 2/2013 | Jimenez et al. |
| 2013/0144388 A1 | 6/2013 | Emery et al. |
| 2013/0158664 A1 | 6/2013 | Palmatier et al. |
| 2013/0197642 A1 | 8/2013 | Ernst |
| 2013/0317615 A1 | 11/2013 | Jimenez et al. |
| 2014/0012383 A1 | 1/2014 | Triplett et al. |
| 2014/0018924 A1 | 1/2014 | McManus et al. |
| 2014/0039622 A1 | 2/2014 | Glerum et al. |
| 2014/0058512 A1* | 2/2014 | Petersheim ............ A61F 2/4455 623/17.16 |
| 2014/0088714 A1 | 3/2014 | Miller et al. |
| 2014/0140757 A1 | 5/2014 | Jimenez et al. |
| 2014/0156007 A1 | 6/2014 | Pabst et al. |
| 2014/0194991 A1 | 7/2014 | Jimenez |
| 2014/0236296 A1 | 8/2014 | Wagner et al. |
| 2014/0249629 A1 | 9/2014 | Moskowitz et al. |
| 2014/0277490 A1* | 9/2014 | Perloff ................ A61F 2/4425 623/17.16 |
| 2014/0343608 A1 | 11/2014 | Whiton et al. |
| 2015/0018951 A1 | 1/2015 | Leobl |
| 2015/0088258 A1 | 3/2015 | Jimenez et al. |
| 2015/0100128 A1 | 4/2015 | Glerum et al. |
| 2015/0148908 A1 | 5/2015 | Marino et al. |
| 2015/0230929 A1* | 8/2015 | Lorio ...................... A61F 2/447 623/17.16 |
| 2015/0272743 A1 | 10/2015 | Jimenez et al. |
| 2015/0272745 A1* | 10/2015 | Jimenez ................ E05F 1/00 623/17.16 |
| 2015/0272746 A1 | 10/2015 | Jimenez et al. |
| 2015/0351925 A1 | 12/2015 | Emerick et al. |
| 2016/0262907 A1 | 9/2016 | Jimenez |
| 2016/0356368 A1 | 12/2016 | Jimenez et al. |
| 2017/0056200 A1* | 3/2017 | Koch ........................ A61F 2/44 |

FOREIGN PATENT DOCUMENTS

| | | |
|---|---|---|
| EP | 1881209 A1 | 1/2008 |
| FR | 2372998 A1 | 12/1976 |
| JP | 05-81194 | 4/1993 |
| JP | 2004-301135 A | 10/2004 |
| JP | 2008-208932 A | 9/2008 |
| WO | WO 2004/026188 A2 | 4/2004 |
| WO | WO 2004/109155 A1 | 12/2004 |
| WO | WO 2005/081330 A2 | 9/2005 |
| WO | WO 2005/096975 A2 | 10/2005 |
| WO | WO 2006/094535 A1 | 9/2006 |
| WO | WO 2006/116052 A1 | 11/2006 |
| WO | WO 2006/125329 A1 | 11/2006 |
| WO | WO 2007/002583 A2 | 1/2007 |
| WO | WO 2007/009107 A2 | 1/2007 |
| WO | WO 2007/028140 A2 | 3/2007 |
| WO | WO 2007/076377 A2 | 7/2007 |
| WO | WO 2007/111979 A2 | 10/2007 |
| WO | WO 2008/137192 A1 | 11/2008 |
| WO | WO 2009/018349 A2 | 2/2009 |
| WO | WO 2010/078468 A2 | 7/2010 |
| WO | WO 2010/078520 A2 | 7/2010 |
| WO | WO 2011/011609 A2 | 1/2011 |
| WO | WO 2011/011626 A2 | 1/2011 |
| WO | WO 2014/066890 A1 | 5/2014 |

OTHER PUBLICATIONS

PCT/US2010/042915, filed Jul. 22, 2010, Search Report and Written Opinion dated Apr. 22, 2011.
PCT/US2009/069876, filed Dec. 30, 2009, International Search Report and Written Opinion dated Sep. 27, 2010, 10 pages.
PCT/US2009/069958, filed Dec. 31, 2009, International Search Report and Written Opinion dated Nov. 29, 2010, 7 pages.
PCT/US2015/055449, filed Oct. 14, 2015, International Search Report and Written Opinion dated Dec. 11, 2015, 9 pages.
PCT/US2015/032977, filed May 28, 2015, International Search Report and Written Opinion dated Sep. 21, 2015, 10 pages.

(56) References Cited

OTHER PUBLICATIONS

European Application No. EP 09837185.9, European Search Report dated May 14, 2013, 7 pages.
Japanese Application No. 2012-521784, JP Office Action dated Feb. 18, 2014, 8 pages.
PCT/US2013/067070, PCT Written Opinion/Search Report dated Feb. 27, 2014, 14 pages.
PCT/US2014/052913, PCT Written Opinion/Search Report dated Dec. 22, 2014, 10 pages.
European Application No. EP 10802916.6, Examination Report dated May 12, 2016, 4 pages.
Canadian Application No. 2,768,867, Office Action dated Aug. 4, 2016, 4 pages.
Canadian Application No. 2,768,867, Office Action dated Apr. 19, 2017, 4 pages.
European Application No. EP14887838.2, Extended European Search Report, dated Oct. 25, 2017, 8 pages.
Wenzel Spine, Inc., VariLift®-L Expandable Interbody Fusion Device: A proven solution for stand-alone fusion, Product Overview, 12 pages, 2010.
Peter A. Halverson, et. al., Tension-based Multi-stable Compliant: Rolling-contact Elements, Department of Mechanical Engineering, Brigham Young University, Provo UT, USA 84602, 34 pages, 2007.
Just L. Herder, Force Directed Design of Laparoscopic Forceps, ASME Design Engineering Technical Conference, 8 pages, 1998.
Alexander H. Slocum, Fundamentals of Design, 2005.
W. Küsswetter, A Supplementary Instrumentation for Posterior Fusion of Spine in Scoliosis, Archives of Orthopedic Traumatic Surgery, 1980, 1 page.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.
Amelie Jeanneau, et. al., A Compliant Rolling Contact Joint and its Application in a 3-DOF Planar Parallel Mechanism with Kinematic Analysis, ASME, Design Engineering Technical Conferences, 9 pages, 2004.
Hunter et al., Overview of Medical Devices, Department of Radiology, University of Arizona, Aug. 2001, pp. 89-140, vol. 30, No. 4, ISSN: 0363-0188.
Medtronic Sofamor Danek USA, Inc., CAPSTONE Instrument Set Technique, http://www.mtortho.com/public/capstone.pdf, © 2005, 25 pages.
Medtronic, CAPSTONE PEEK Spinal System Surgical Technique, http://www.mtortho.com/public/capstone_peek_st.pdf, © 2009, 36 pages.
Website printout from https://seelio.com/w/fgf/omnilif-the-new-standard-in-spinal-deformity-correction-and-fusion?student=lumbarjax; dated Nov. 27, 2014, 5 pages.
Printout from Video for OmniLIF Anterior Insertion Approach from Lumber Jax; https://seelio.com/w/fgf/omnilif-the-new-standard-in-spinal-deformity-correction-and-fusion?student=lumbarjax; dated Nov. 27, 2014, 7 pages.
Printout from Video for OmniLIF Features from Lumber Jax; https://seelio.com/w/fgf/omnilif-the-new-standard-in-spinal-deformity-correction-and-fusion?student=lumbarjax; dated Nov. 27, 2014, 11 pages.
Application and File History for U.S. Appl. No. 12/407,608, filed Mar. 19, 2009, now U.S. Pat. No. 8,628,577, Inventors Jimenez et al.
Application and File History for U.S. Appl. No. 12/650,994, filed Dec. 31, 2009, now U.S. Pat. No. 8,523,944, Inventors Jimenez et al.
Application and File History for U.S. Appl. No. 12/651,266, filed Dec. 31, 2009, now U.S. Pat. No. 8,540,452, Inventors Jimenez et al.
Application and File History for U.S. Appl. No. 12/841,465, filed Jul. 22, 2010, now U.S. Pat. No. 8,303,663, Inventors Jimenez et al.
Application and File History for U.S. Appl. No. 12/841,869, filed Jul. 22, 2010, Now U.S. Pat. No. 9,358,125, Inventors Jimenez et al.
Application and File History for U.S. Appl. No. 13/189,410, filed Jul. 22, 2011, now U.S. Pat. No. 8,636,746, Inventor Jimenez.
Application and File History for U.S. Appl. No. 13/661,534, filed Oct. 26, 2012, now U.S. Pat. No. 8,932,302, Inventor Jimenez.
Application and File History for U.S. Appl. No. 13/591,463, filed Aug. 22, 2012, now U.S. Pat. No. 8,771,360, Inventor Jimenez.
Application and File History for U.S. Appl. No. 13/891,356, filed May 10, 2013, now U.S. Pat. No. 8,906,100, Inventor Jimenez et al.
Application and File History for U.S. Appl. No. 14/024,764, filed Sep. 12, 2013, now U.S. Pat. No. 9,381,092, Inventor Jimenez et al.
Application and File History for U.S. Appl. No. 14/153,281, filed Jan. 13, 2014, now U.S. Pat. No. 9,867,717, Inventor Jimenez.
Application and File History for U.S. Appl. No. 14/563,660, filed Dec. 8, 2014, now U.S. Pat. No. 9,445,917, Inventor Jimenez et al.
Application and File History for U.S. Appl. No. 14/242,451, filed Apr. 1, 2014, now U.S. Pat. No. 8,940,049, Inventor Jimenez et al.
Application and File History for U.S. Appl. No. 14/318,196, filed Jun. 27, 2014, now U.S. Pat. No. 9,474,626, Inventor Jimenez et al.
Application and File History for U.S. Appl. No. 14/592,507, filed Jan. 8, 2015, now U.S. Pat. No. 9,498,270, Inventor Jimenez et al.
Application and File History for U.S. Appl. No. 14/585,544, filed Dec. 30, 2014, now U.S. Pat. No. 9,486,328, Inventor Jimenez et al.
Application and File history for U.S. Appl. No. 15/164,498, filed May 25, 2016, now U.S. Pat. No. 9,668,879, Inventors: Jimenez et al.
Application and File history for U.S. Appl. No. 15/174,454, filed Jun. 6, 2016, now U.S. Pat. No. 10,117,757. Inventors: Jimenez et al.
Application and File history for U.S. Appl. No. 15/332,066, filed Oct. 24, 2016. Inventors: Jimenez et al.
Application and File history for U.S. Appl. No. 15/591,214, filed May 10, 2017. Inventors: Jimenez et al.
Application and File history for U.S. Appl. No. 15/198,557, filed June 30, 2016, now U.S. Pat. No. 10,060,469, Inventors: Jimenez et al.
Application and File history for U.S. Appl. No. 16/184,509, filed Nov. 8, 2018. Inventors: Jimenez et al.
Application and File history for U.S. Appl. No. 16/750,784, filed Jan. 23, 2020. Inventors: Jimenez et al.
Application and File history for U.S. Appl. No. 16/574,265, filed Sep. 18, 2019. Inventors: Jimenez et al.
International Search Report and Written Opinion for International Application No. PCT/US2019/068890 dated Apr. 29, 2020.

* cited by examiner

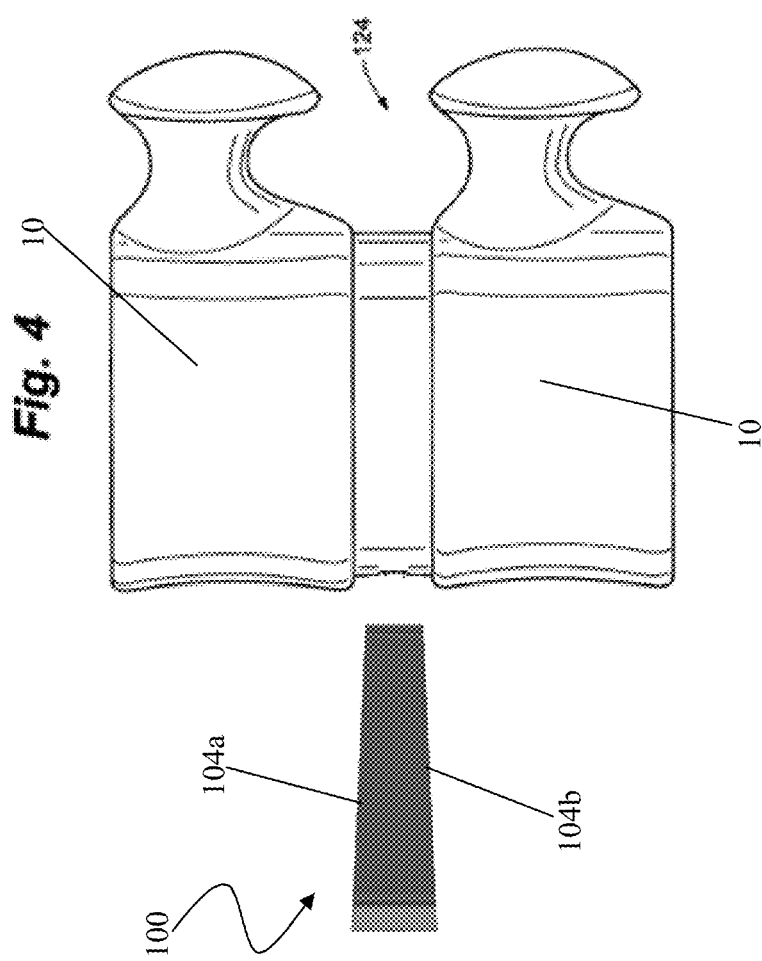

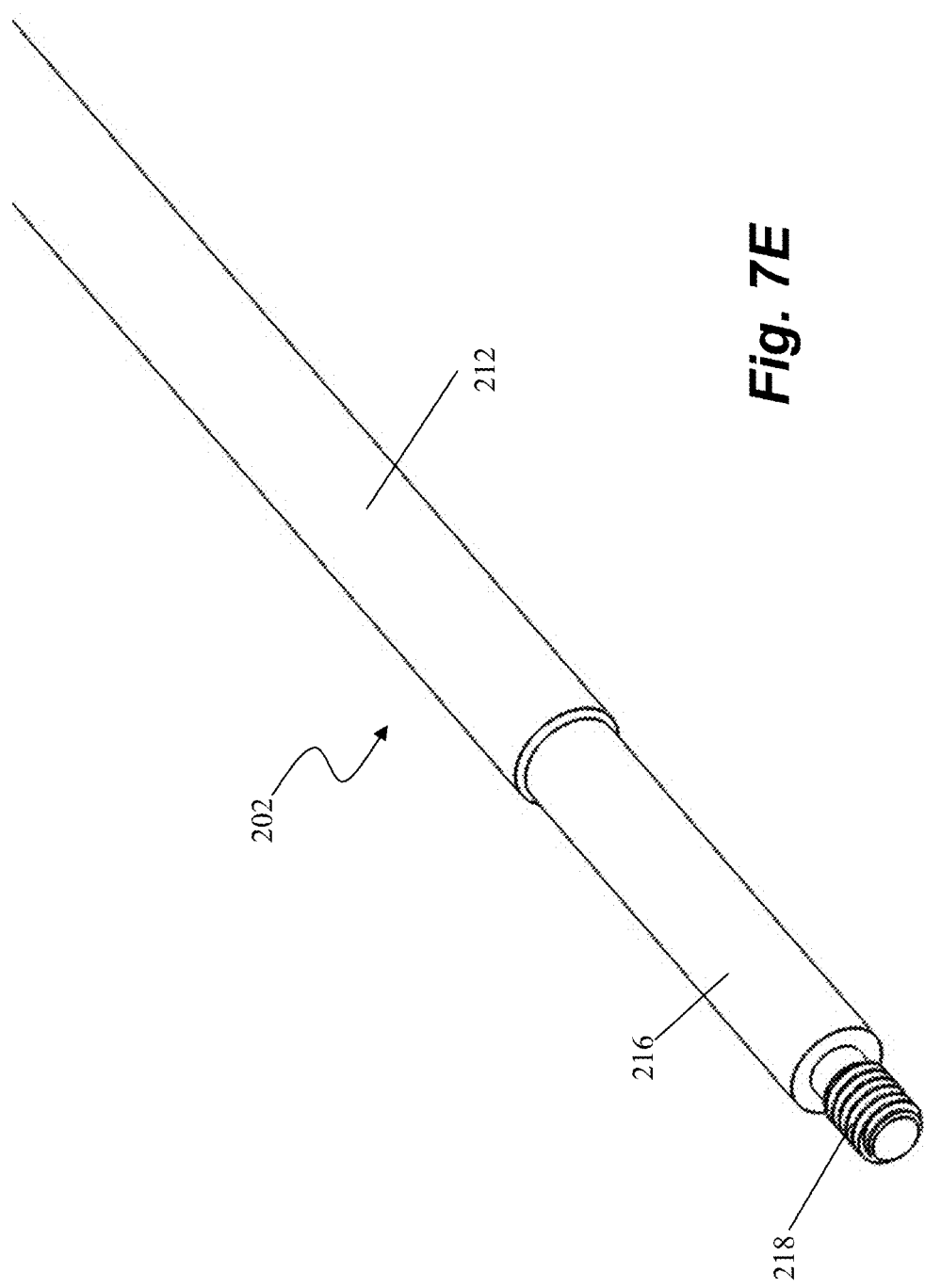

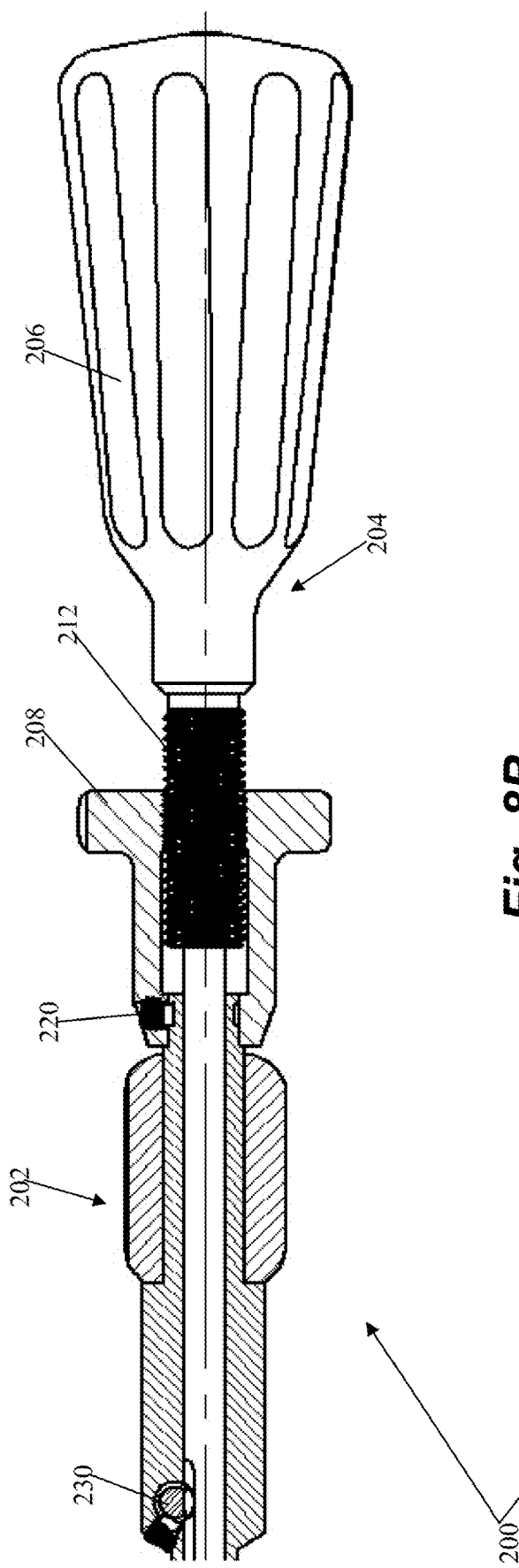
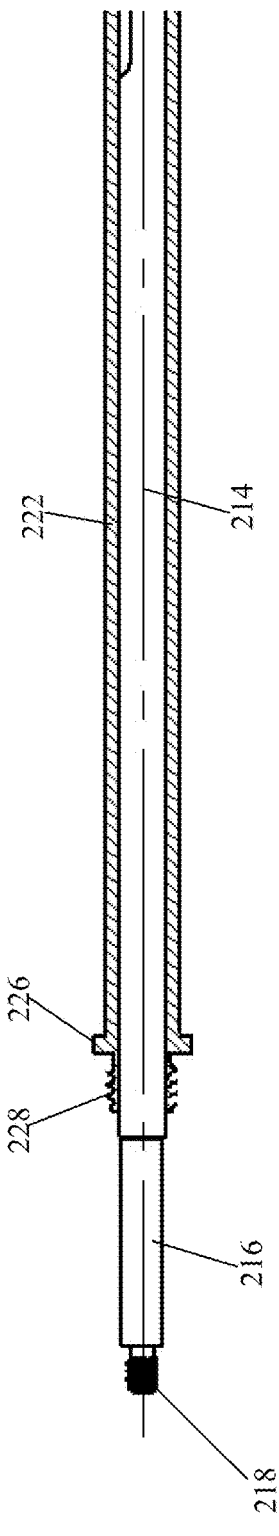
Fig. 8B
Fig. 8C

TRANSVERSELY EXPANDABLE MINIMALLY INVASIVE INTERVERTEBRAL CAGE

TECHNICAL FIELD

The present invention relates to the fusion of vertebral bodies. More specifically, the present invention relates to devices and associated methods for fusion of vertebral bodies that provide robust spinal support in a less invasive manner.

BACKGROUND

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce a distraction device that will distract a collapsed disc in a generally axial direction, decompress the nerve root, and allow load sharing to enhance bone formation, and then implant an intervertebral fusion device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space such that the vertebral bodies are separated in a generally axial direction by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral distraction and fusion can be performed through anterior, posterior, oblique, and lateral approaches. Each approach has its own anatomical challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

As with all minimally invasive surgeries, a primary goal is to provide equivalent or near equivalent treatment as more invasive surgical techniques but with less discomfort, recovery time, etc. for the patient. One problem with minimally invasive intervertebral fusion procedures is that the limited size of the surgical access limits the size of the implant(s) that can be inserted. While devices that are vertically expandable in a generally axial direction have addressed some of these issues by being able to be inserted through a smaller opening and then made taller in a generally axial direction within the disc space, such devices are still limited in the transverse footprint that can be covered within the disc space which can affect the stability of the device within the disc space and limits the area for bone grown.

SUMMARY

Disclosed herein are systems and methods for intervertebral body fusion that provide more robust support within the disc space. Intervertebral body fusion devices can have a unitary monolithic body including a plurality of body segments interconnected with each other by flexure members. Devices be configured to be inserted through an opening in a compressed configuration and then expanded within the disc space to an expanded configuration. In the expanded configuration, devices can have a greater mediolateral or transverse to the disc space footprint. This wider footprint provides greater support for the vertebrae relative to the size of the opening through which the device is inserted.

In one embodiment, an expandable intervertebral body fusion device includes a unitary monolithic body having a plurality of body segments connected to each other with flexure members and an opening defined between the plurality of body segments. The device body can include an anterior body segment, a posterior body segment and one or more mediolateral body segments extending between the anterior body segment and the posterior body segment along both a lateral side and a medial side of the anterior body segment and the posterior body segment. A threaded opening can be formed in one or more of the anterior body segment and the posterior body segment. The body is configured to be mediolaterally expanded from a compressed configuration to an expanded configuration by interaction of an expansion tool with the threaded opening causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration.

In one embodiment, a transversely expandable intervertebral body fusion device for a disc space between adjacent vertebra of a spine of a human patient includes a unitary monolithic body configured in size and shape to be implantable in the disc space. The body can have at least four body segments each connected to adjacent body segments by one or more flexure members with the body segments surrounding and collectively defining an opening within a transverse plane bisecting the body. The body segments can include an anterior body segment, a posterior body segment and at least one mediolateral body segment extending between the anterior body segment and the posterior body segment along each of a lateral side and a medial side of the body. A threaded opening can be formed in at least one of the anterior body segment and the posterior body segment. The body can be configured to be mediolaterally expanded from a transversely compressed configuration to a transversely expanded configuration by interaction of an expansion tool with the threaded opening causing the at least one mediolateral body segments on each side to generally move transversely away from each other, thereby expanding the opening of the body and forming a perimeter defined by an outer edge of the body that presents a mediolateral footprint in the expanded configuration that is greater than in the compressed configuration.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 4 depicts a schematic representation of an expandable intervertebral body fusion device according to an embodiment being inserted between vertebrae of a patient.

FIGS. 7A-7F depict portions of an insertion device for an expandable intervertebral body fusion device according to an embodiment.

FIGS. 8A-8C depict portions of an insertion device for an expandable intervertebral body fusion device according to an embodiment.

DETAILED DESCRIPTION OF THE DRAWINGS

Figure 1A:
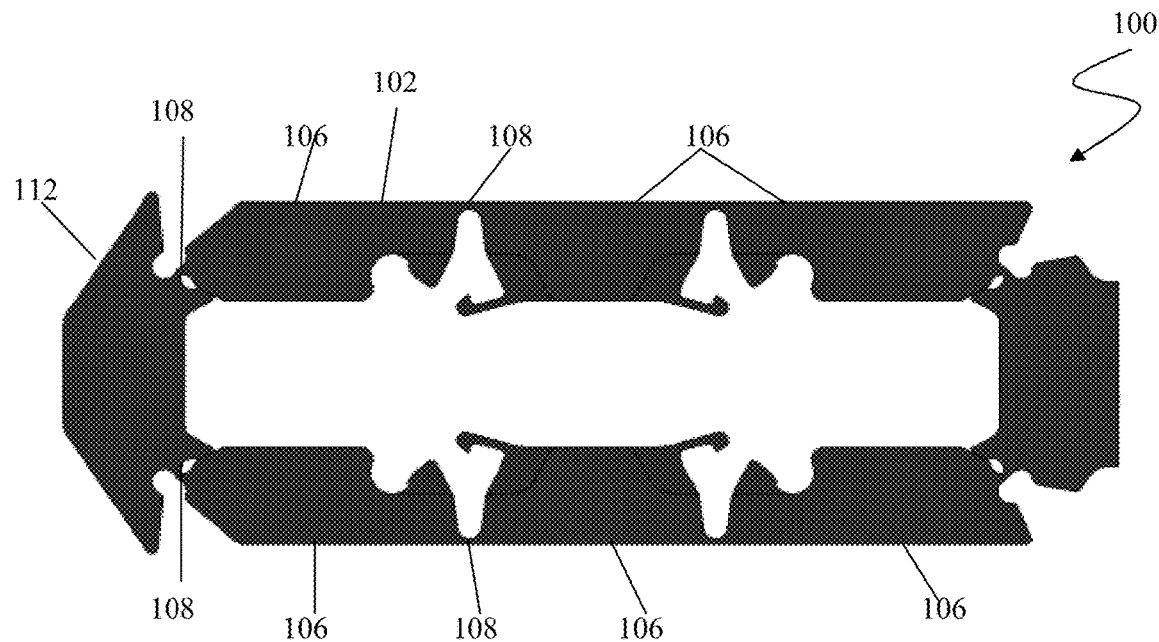
FIGS. 1A-1D depict an expandable intervertebral body fusion device in a collapsed configuration according to an embodiment.
Figure 1B:
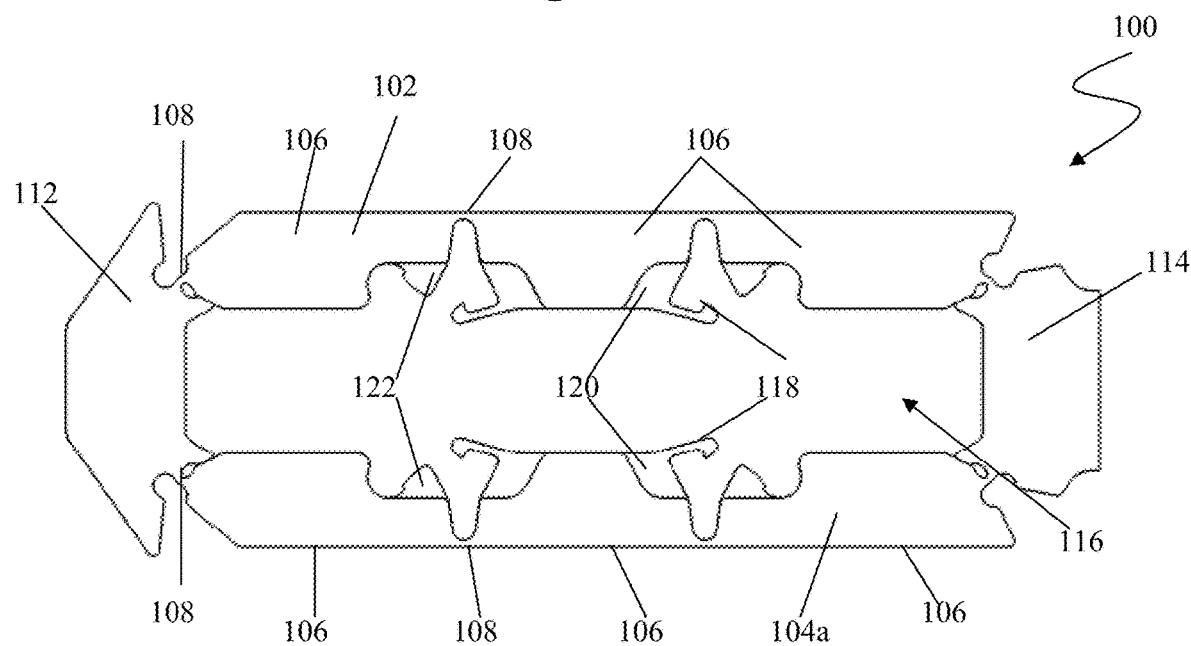
Figure 1C:
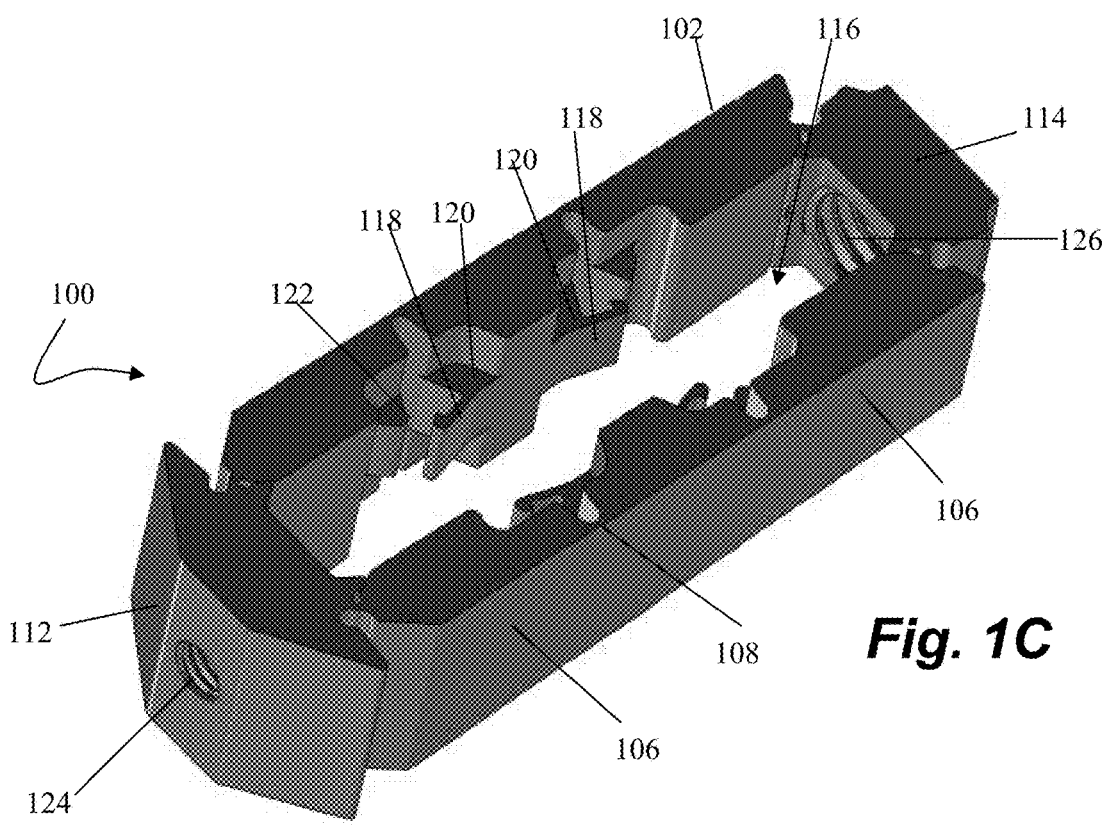
Figure 1D:
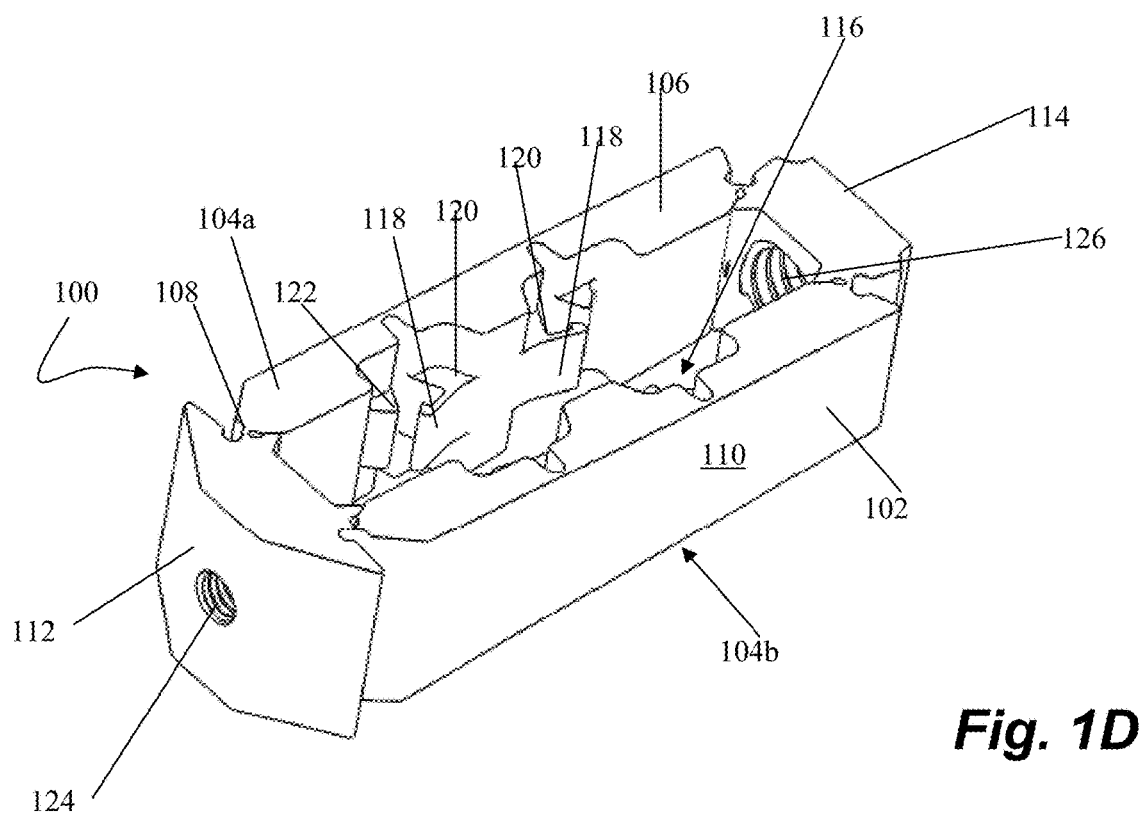
Figure 2B:
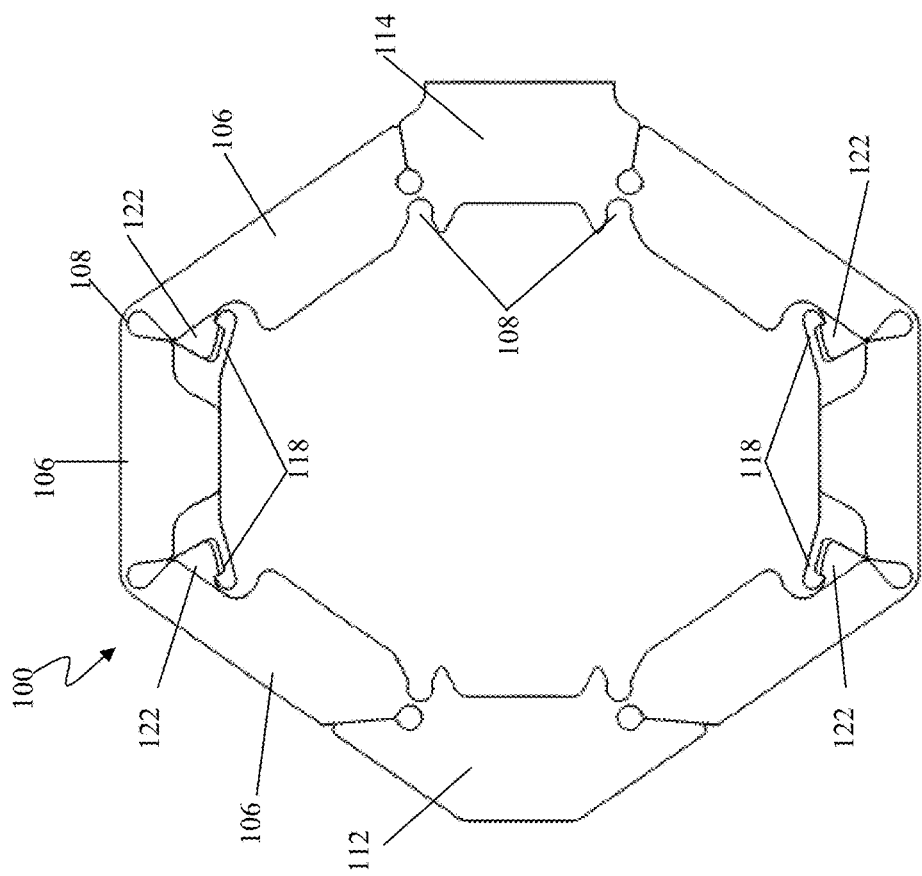
FIGS. 2A-2D depict the expandable intervertebral body fusion device of FIGS. 1A-1D in an expanded configuration.
Figure 2A:
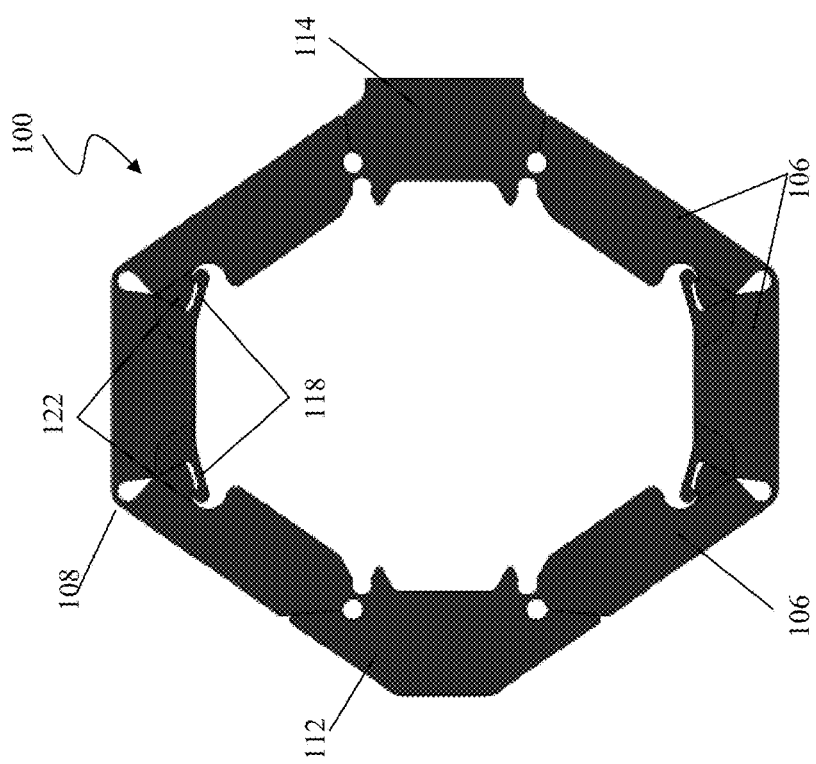
Figure 2D:
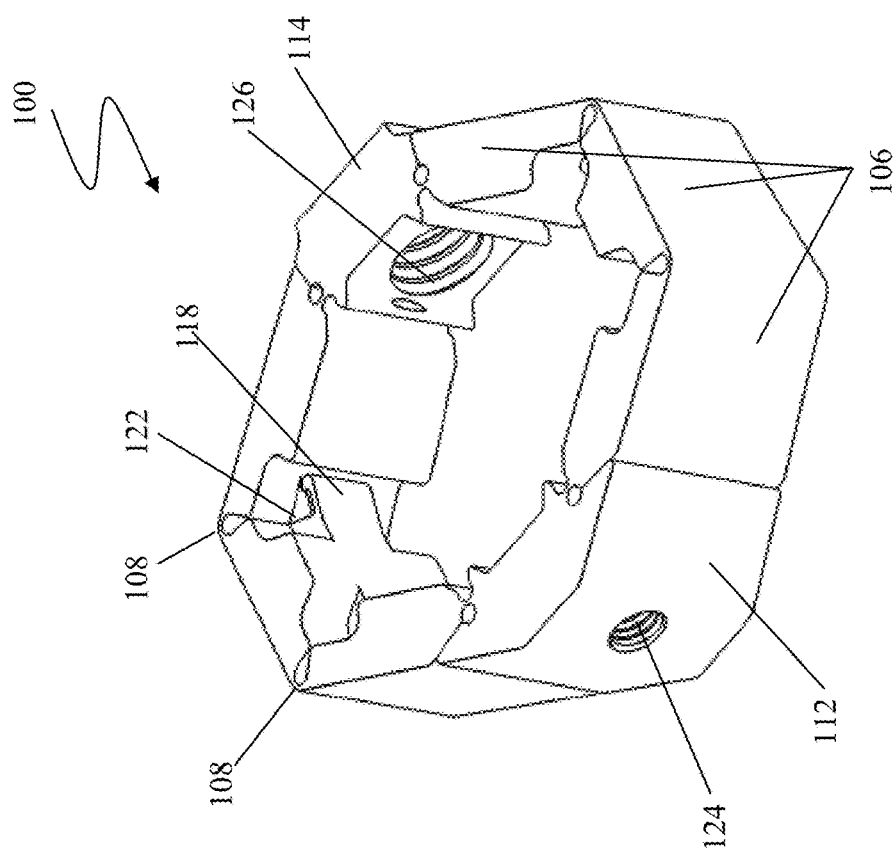
Figure 2C:
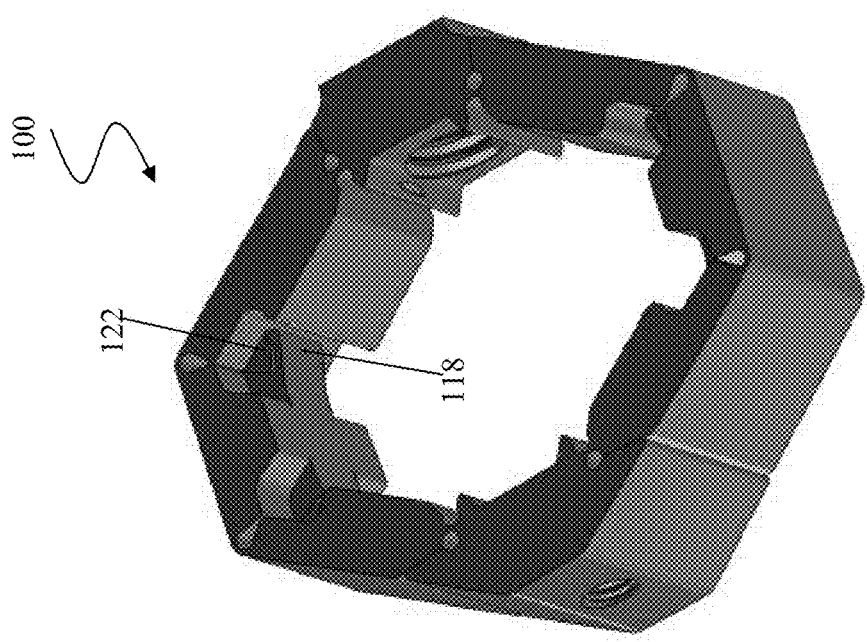

FIGS. 1A-1D and 2A-2D depict an expandable intervertebral body fusion device 100 according to an embodiment. FIGS. 1A-1D depict the device 100 in a collapsed configuration and FIGS. 2A-2D depict the device 100 in an expanded configuration. In practice, the device 100 is inserted into the disc space through a minimally invasive access in the collapsed configuration and then expanded inside of the disc space. In embodiments, the device 100 is inserted between adjacent vertebrae 10 on its side as depicted in FIG. 4 such that when it is expanded in the disc space rather than expanding vertically it expands horizontally/transversely to the disc space to enable the device to take up a larger footprint within the disc space as can be seen contrasting FIG. 5A and FIG. 5B. The device is therefore able to occupy more lateral to medial and anterior to posterior space within the disc space relative to the size of the access that has heretofore been possible. In one embodiment in its insertion and un-expanded state the device is 8 mm in height, 11.5 mm in width and 26 mm in length. The device can have many heights from 8 mm up to 16 mm. In embodiments, the width can go from 8-12 mm and the length from 22 mm-32 mm. When the device is expanded, the height remains the same but the width can double or nearly double (from 11.5 to 22 mm or 47%) and the length goes from 26 mm to 20 mm (16% decrease). The device can have many lordotic angles from 0 to 15 degrees or higher; the most common being 0, 6, 12 degrees. The horizontal top and bottom of the device can have different shapes to better fit the endplates such as football shaped or domed. Also, the different segments of the device separated by flexures could be tailored or cut by wire EDM or 3D printed to create different horizontal expanded states such as oval, elliptical, circular, bean shaped, banana shaped or many other polygons and non-polygon shapes. The mean disc height at the L3-4 level is 11.3 mm+/−1.8 mm, LA-5 11.3+/−2.1 mm and L5-S1 10.7+/−2.1 mm. The average circumference of the L4 endplate is about 141 mm and surface area 1,492 mm$^2$ above. The device can have difference foot prints to try to fill the endplate or disc space circumference.

Referring now to FIGS. 1A-1D, device 100 can include a device body 102. Generally, device body 102 can be unitarily formed as a single monolithic construct, although multiple component embodiments are also contemplated. Device body 102 can include upper 104a and lower 104b bearing surfaces. As noted above, device 100 can be inserted generally on its side such that bearing surfaces 104a, 104b interface with and bear the forces of the adjacent vertebrae 10 (see FIGS. 4 and 5A-5B). In embodiments, the larger threaded opening 126 are positioned dorsal or posterior and the smaller opening 124 is positioned ventral or anterior. Device body 102 can include a plurality of mediolateral body segments 106 unitary connected to each other by flexure 108 comprising a thin, flexible strip of material. As can be seen in, e.g., FIGS. 1C-1D, mediolateral body segments 106 and flexures 108 can perform a continuous, unitary out perimeter surface 110. Device body 102 can further include an anterior body segment 112 and posterior body segment 114. Anterior and posterior body segments 112, 114 can also be connected with mediolateral body segments by flexures 108. Device body 102 further defines an open interior 116 between the body segments.

In the depicted embodiment, the device 100 includes three mediolateral body segments 106 on each side such that the device includes a total of eight body segments. In some embodiments, a device having eight body segments may be generally octagonally shaped in the expanded configuration as depicted in FIGS. 2A-2D. In other embodiments, device may have greater or fewer mediolateral body segments on each side.

Device body 102 can further include a plurality of locking flexures 118 disposed in the open interior 116. As can be seen in, e.g., Figures IC-1D, locking flexures 118 can extend from a lock base 120 that is recessed with respect to bearing surfaces 104a, 104b. As will be described in more detail below, each locking flexure 118 corresponds with locking projection 122 extending from an adjacent body segment 106.

Each of anterior body segment 112 and posterior body segment 114 can include a threaded opening that aids in insertion and expansion of device. In one embodiment, anterior body segment 112 includes an anterior threaded opening 124 configured to interface with a stabilizing element for inserting the device 100 into the disc space. Posterior body segment 114 can include a posterior threaded opening 126 that is larger than anterior opening 124 and can be configured to interface with an expansion element that is rotated to expand device body 112, which will be described in more detail below. In other embodiments, anterior opening 124 may interface with the expansion elements while posterior opening 126 interfaces with the stabilizing element. In some embodiments, anterior body segment 112 can be tapered to facilitate insertion of the device 100 into the disc space through the minimally invasive access opening.

Figure 3A:
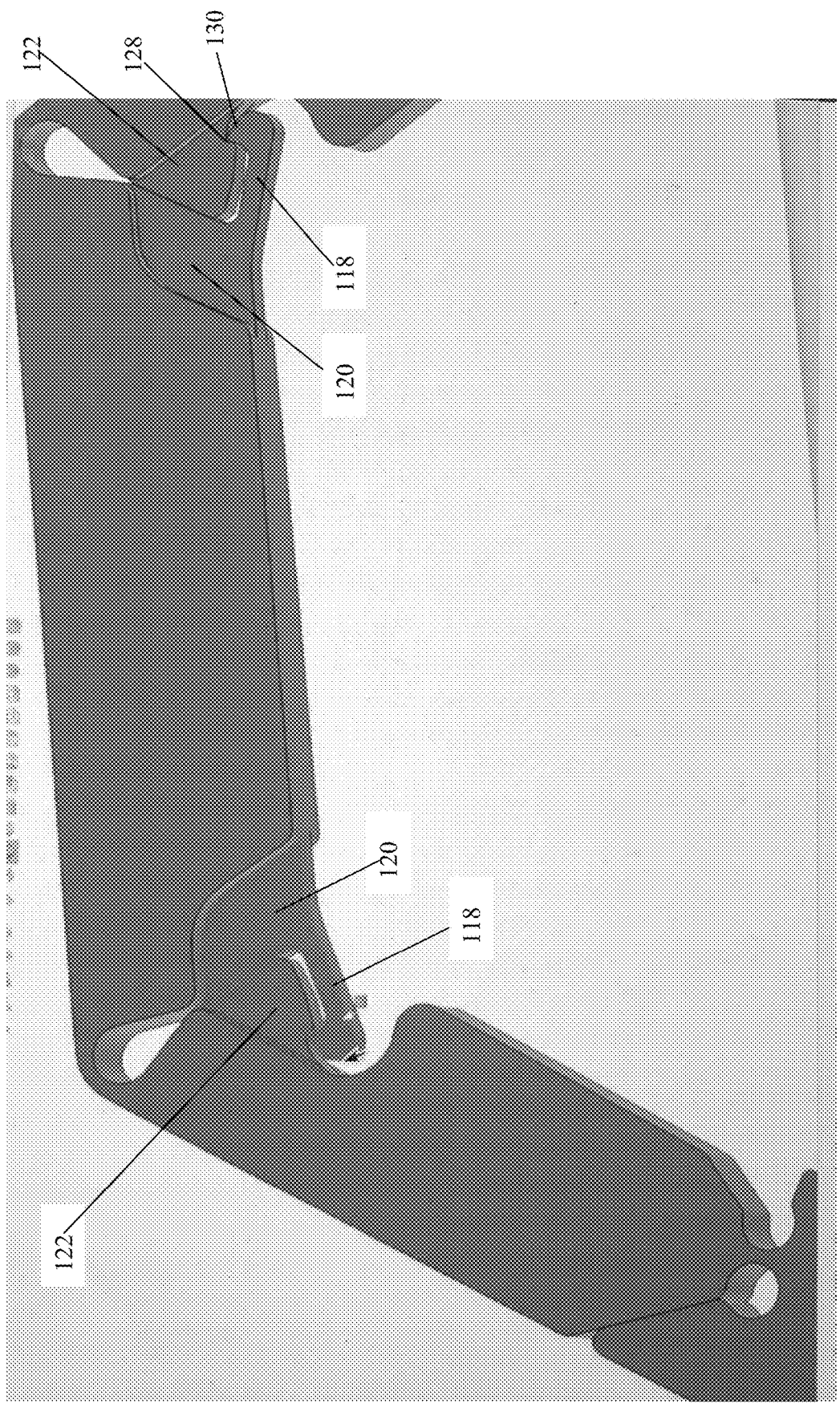
FIGS. 3A-3C depict a portion of the expandable intervertebral body fusion device of FIGS. 2A-2D.
Figure 3B:
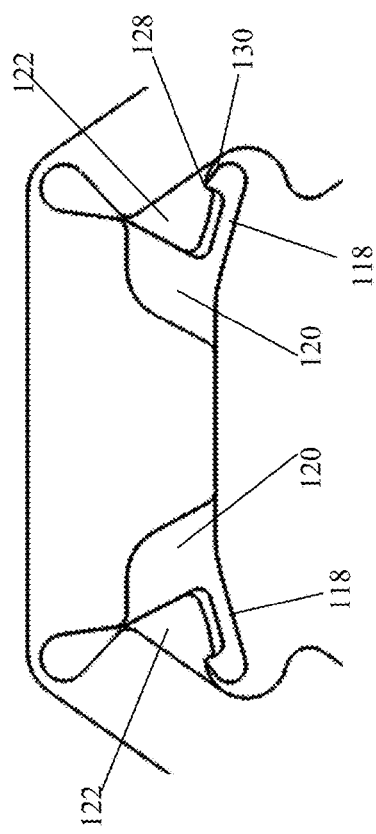
Figure 3C:
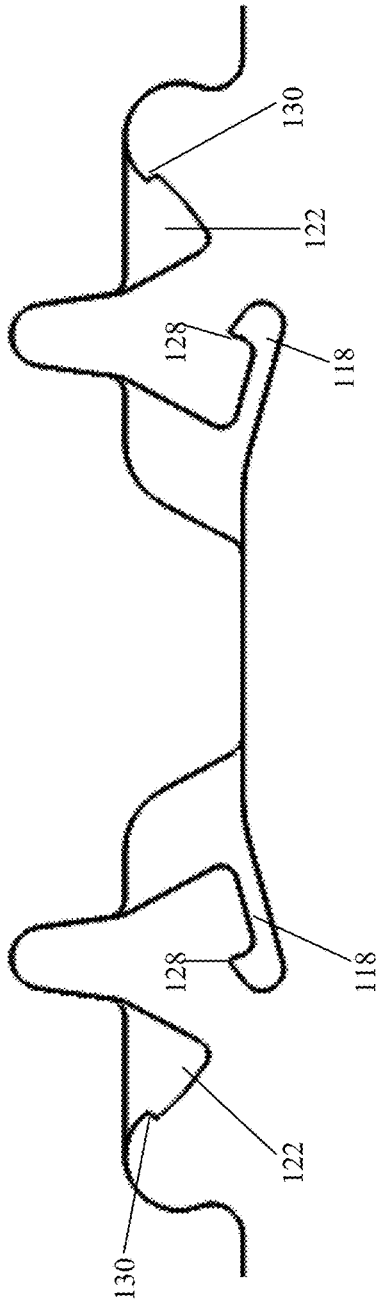

FIGS. 2A-2D depict device 100 in an expanded configuration. As the device 100 is expanded, the mediolateral body segments 106 on opposing sides of the device body 102 are moved away from each other causing the device to expand medially and laterally within the disc space. When the device 100 is expanded, the locking flexures 118 interface and lock with the locking projections 122 to prevent external forces from causes the device to compress from the expanded position following expansion. As can be seen in more detail in FIGS. 3A-3C, each locking flexure 118 includes a pointed tip 128 that interfaces with a notch 130 in locking projections to lock the components together.

Figure 5B:
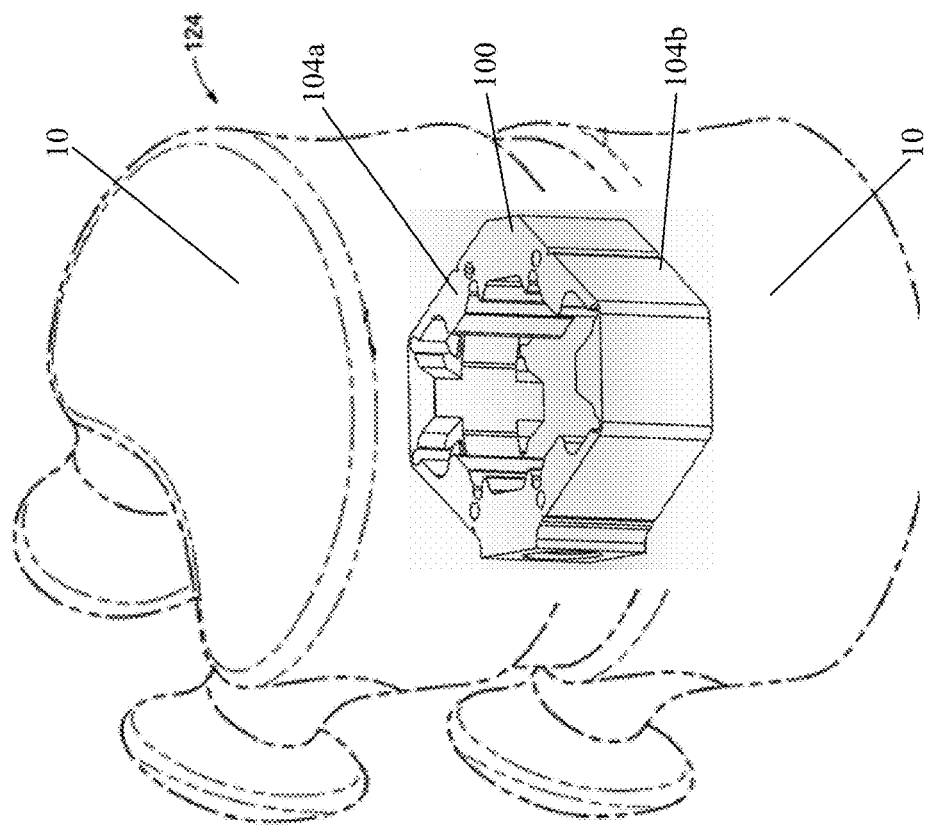
FIGS. 5A-5B depict a schematic representation of an expandable intervertebral body fusion device according to an embodiment inserted between vertebrae of a patient in a compressed and an expanded configuration.
Figure 5A:
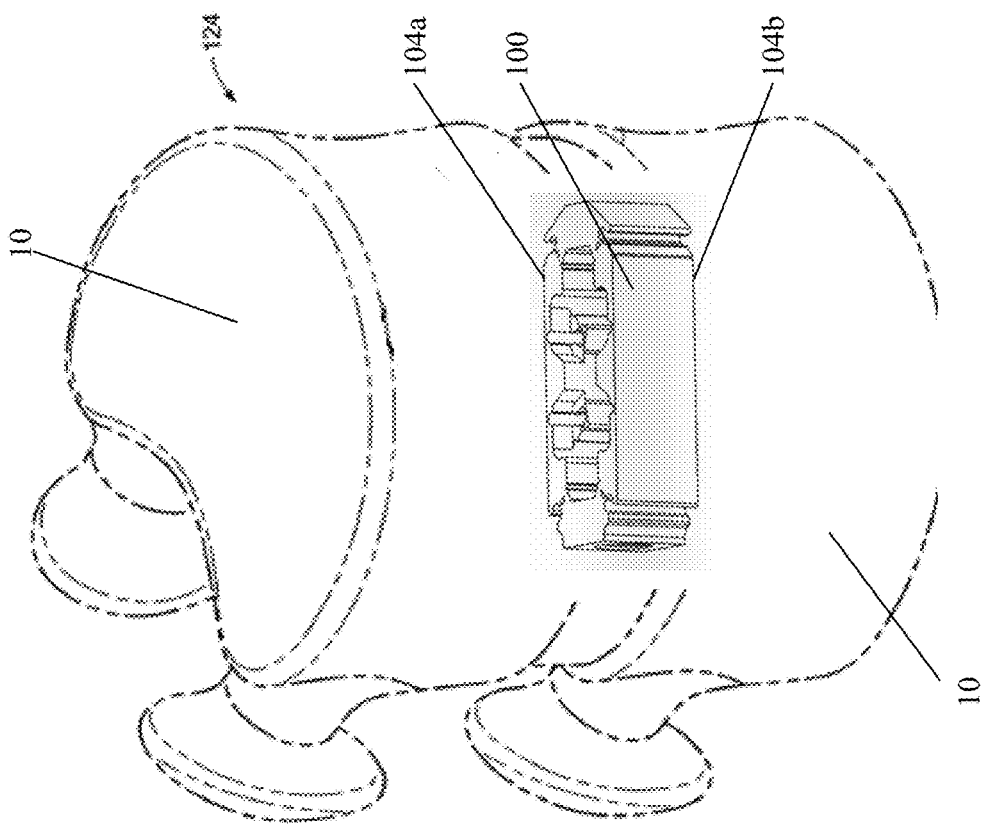

As noted above, in one embodiment device 100 is inserted between adjacent vertebrae 10 on its side, as shown in FIG. 4, with bearing surfaces 104a, 104b configured to interface with the vertebrae. FIGS. 5A-5B depict how the device 100 can be inserted in a collapsed configuration and then expanded within the disc space to occupy a greater footprint within the disc space. Note that these figures show one particular access approach and device orientation relative to the disc space, but that other access approaches and device orientations are possible.

Figure 6A:
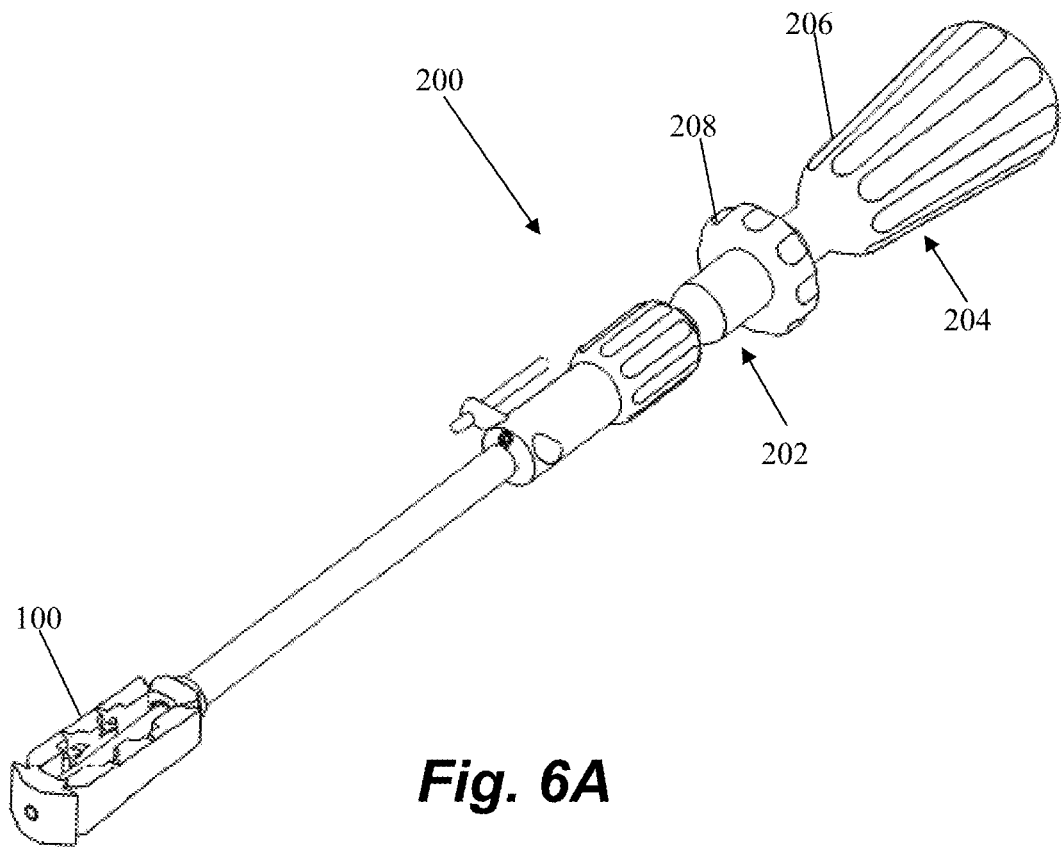
FIGS. 6A-6B depict an expandable intervertebral body fusion device and a corresponding insertion device according to an embodiment.
Figure 6B:
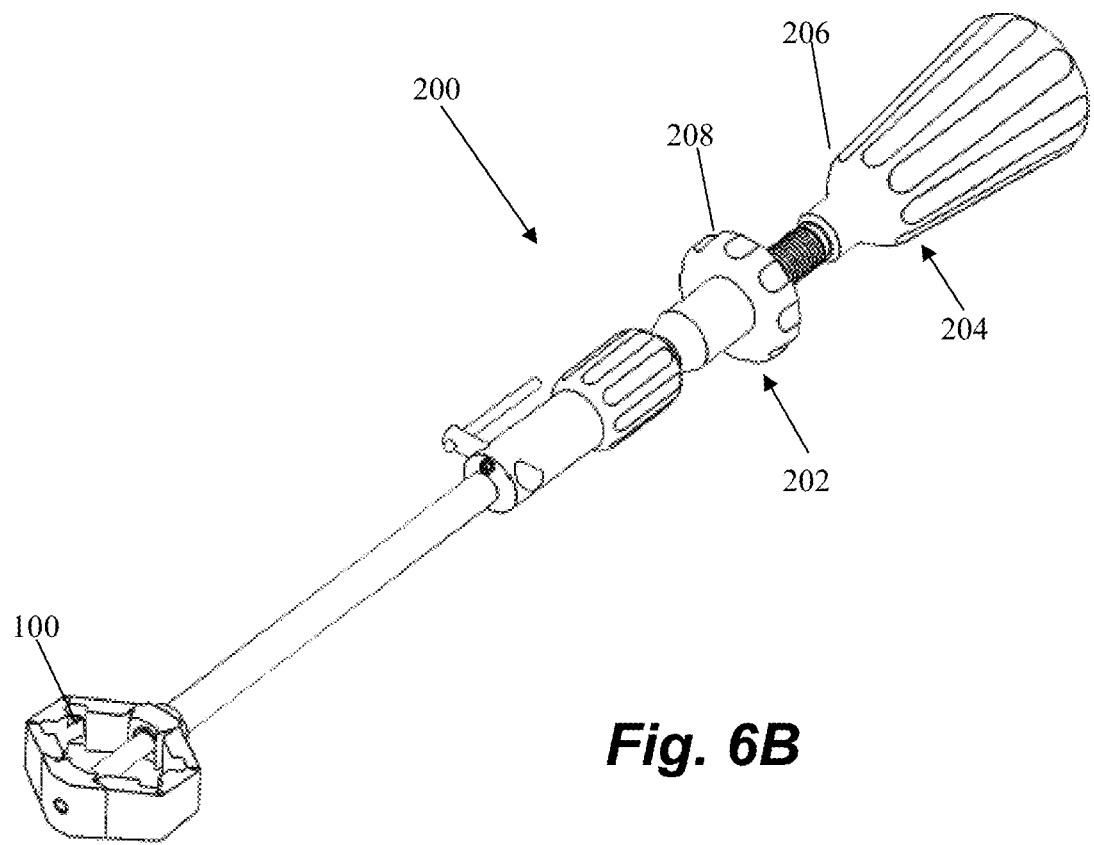
Figure 7A:
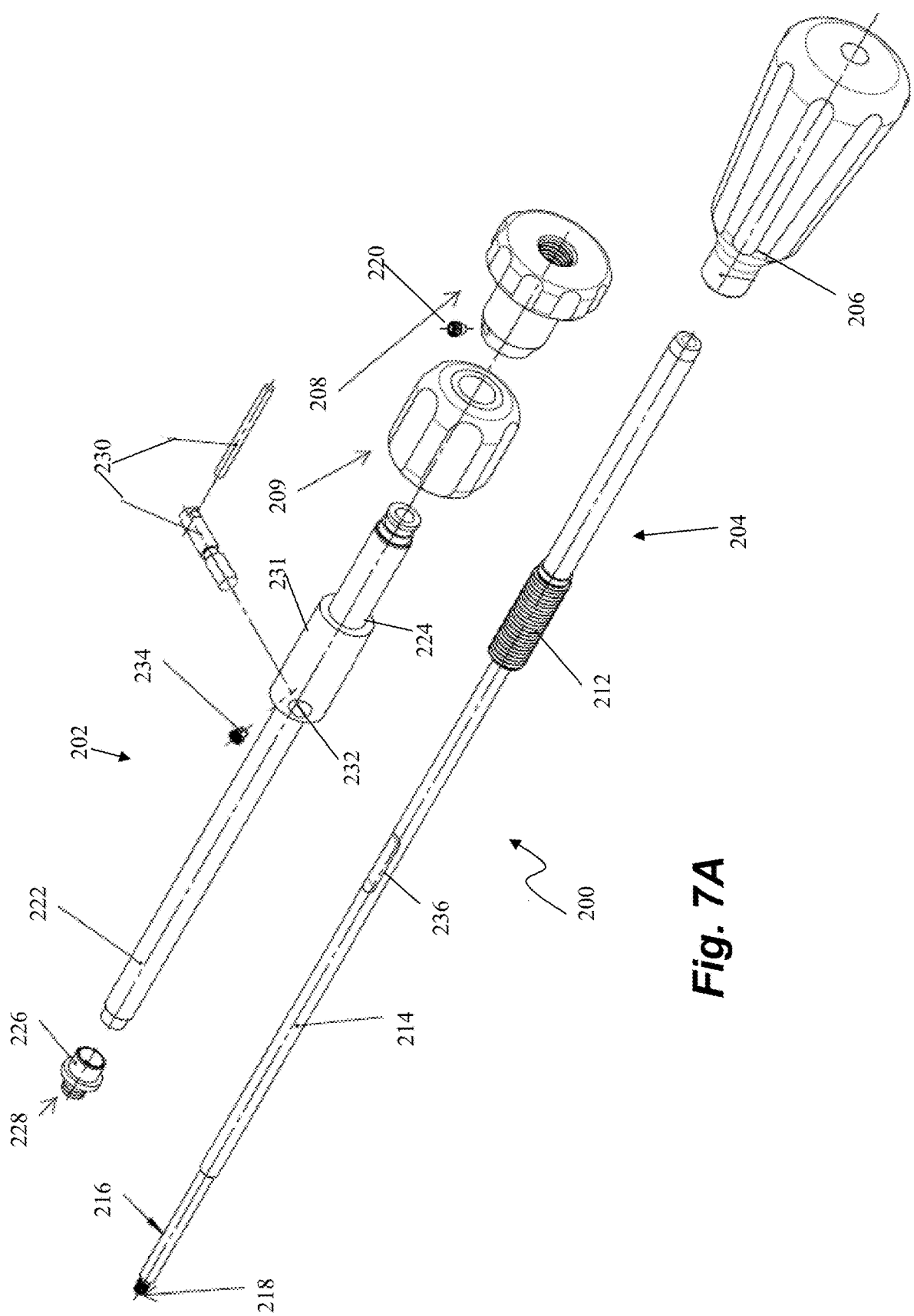
Figure 7B:
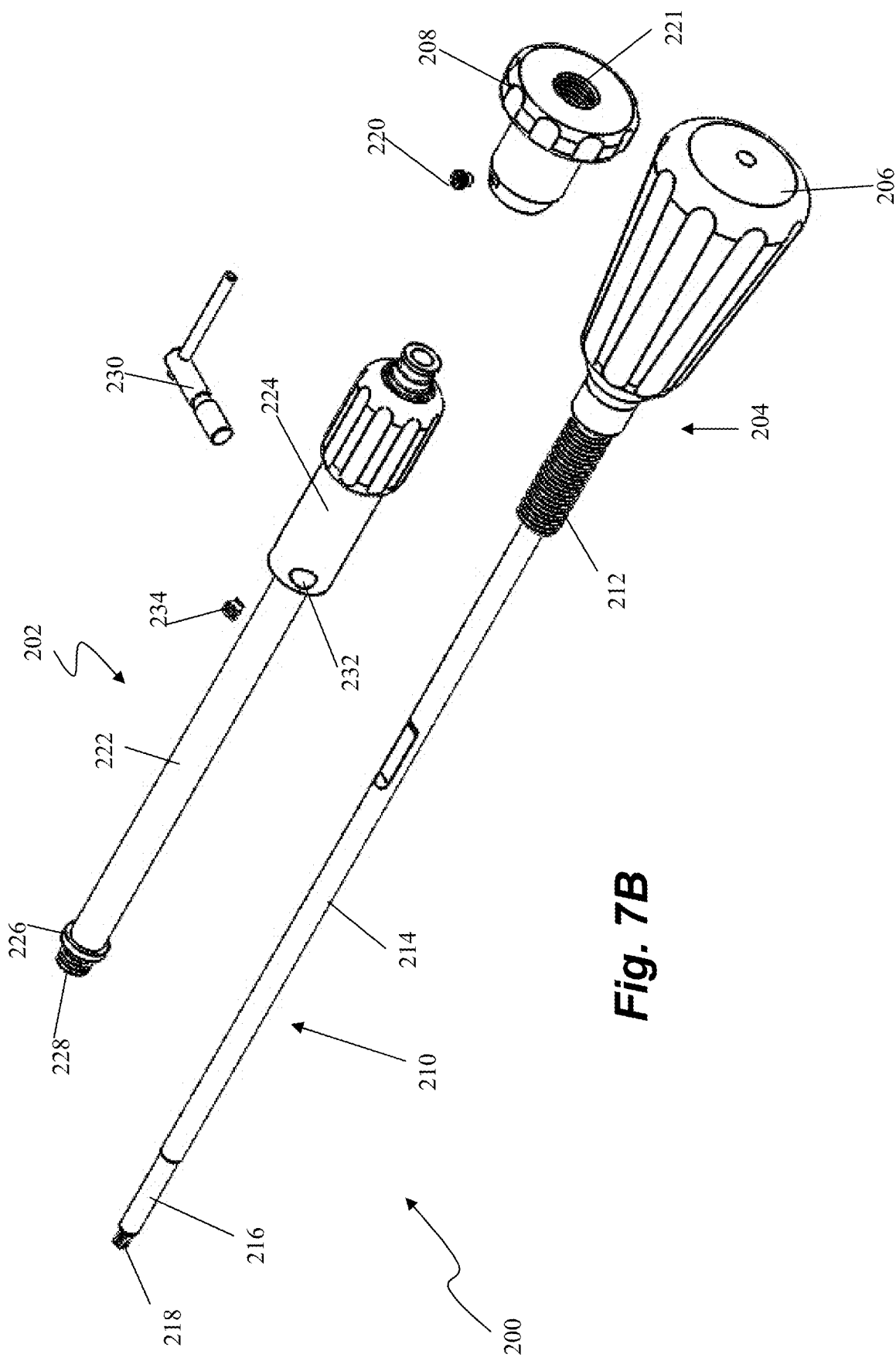
Figure 7C:
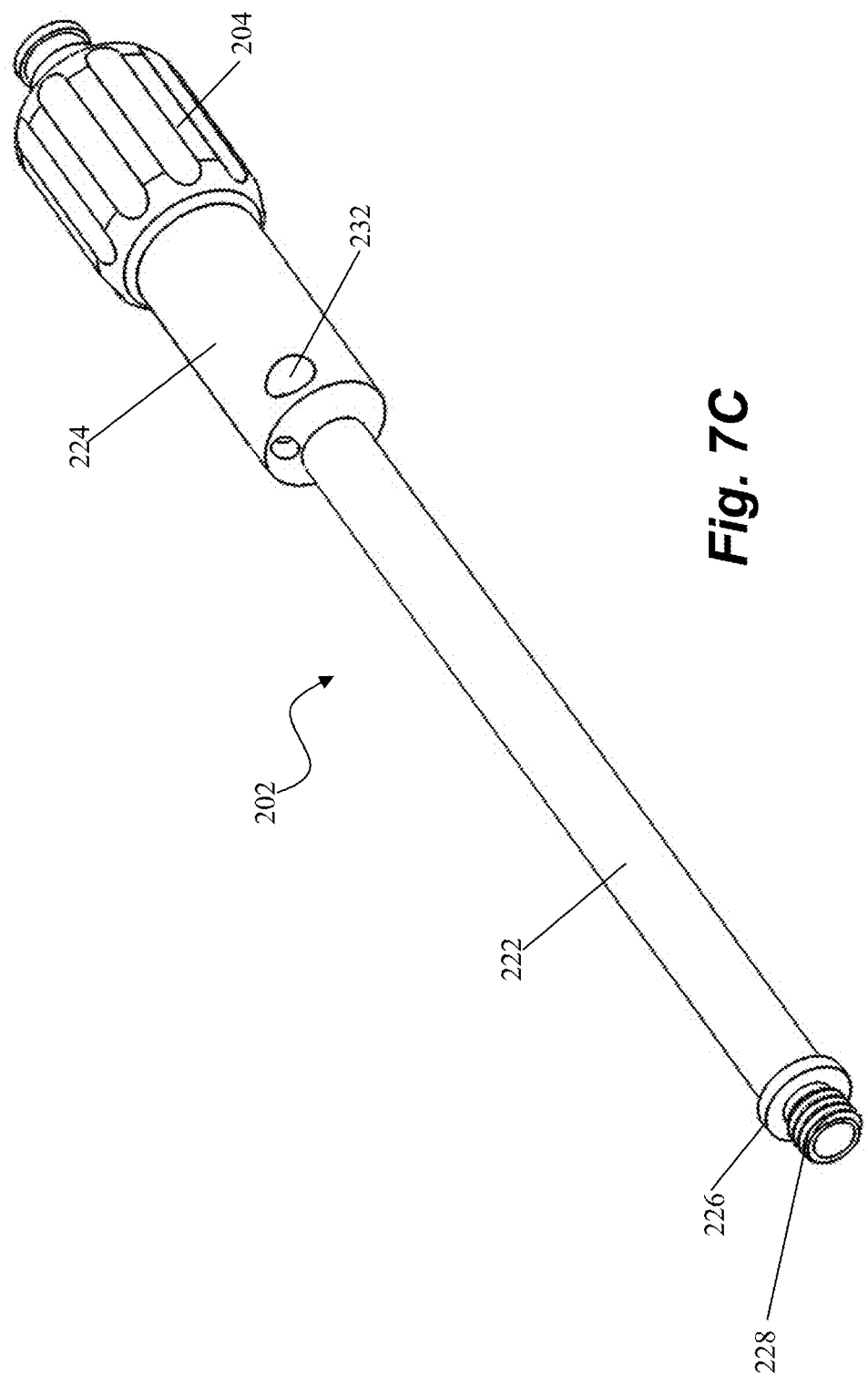
Figure 7D:
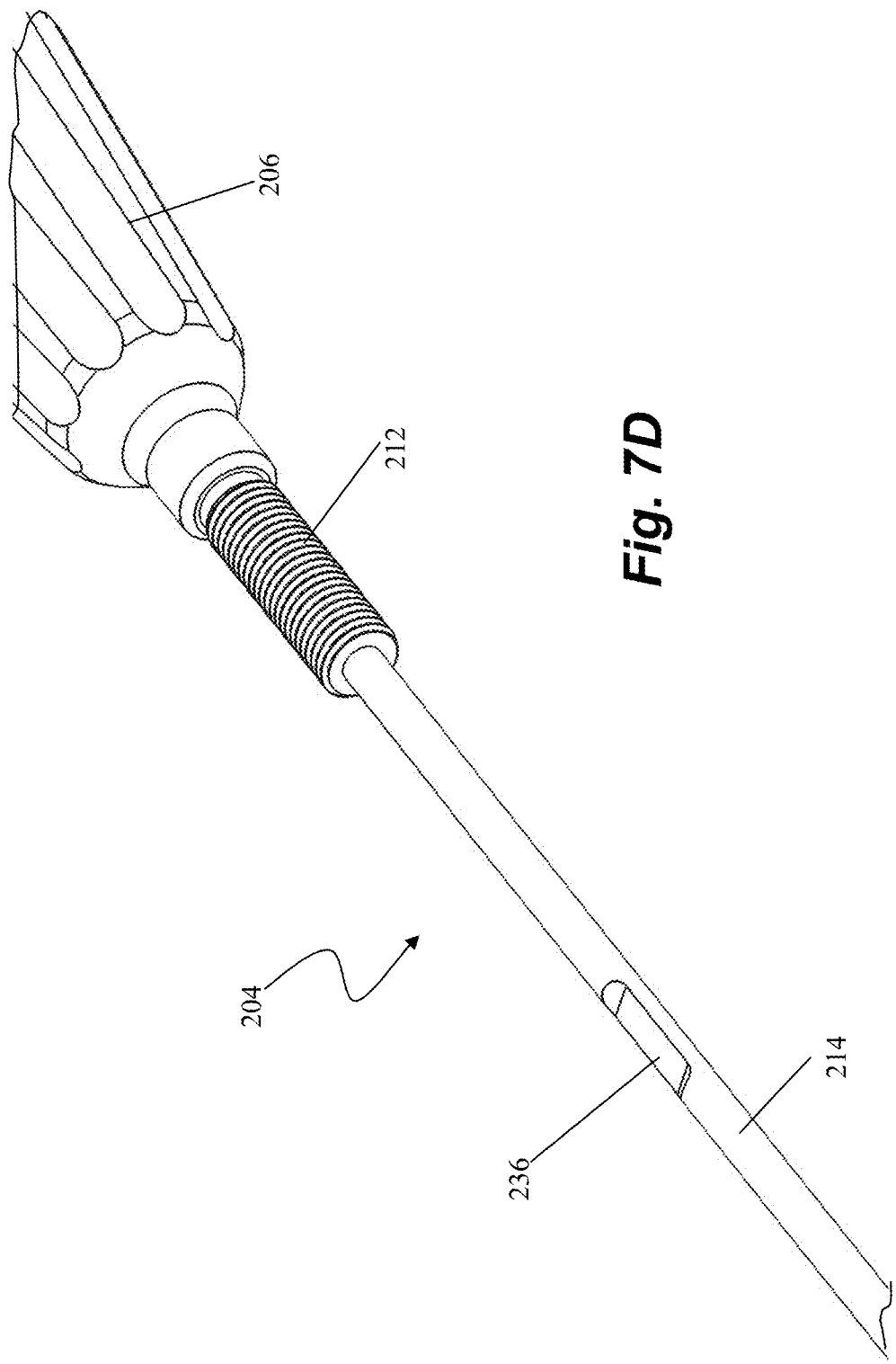
Figure 7F:
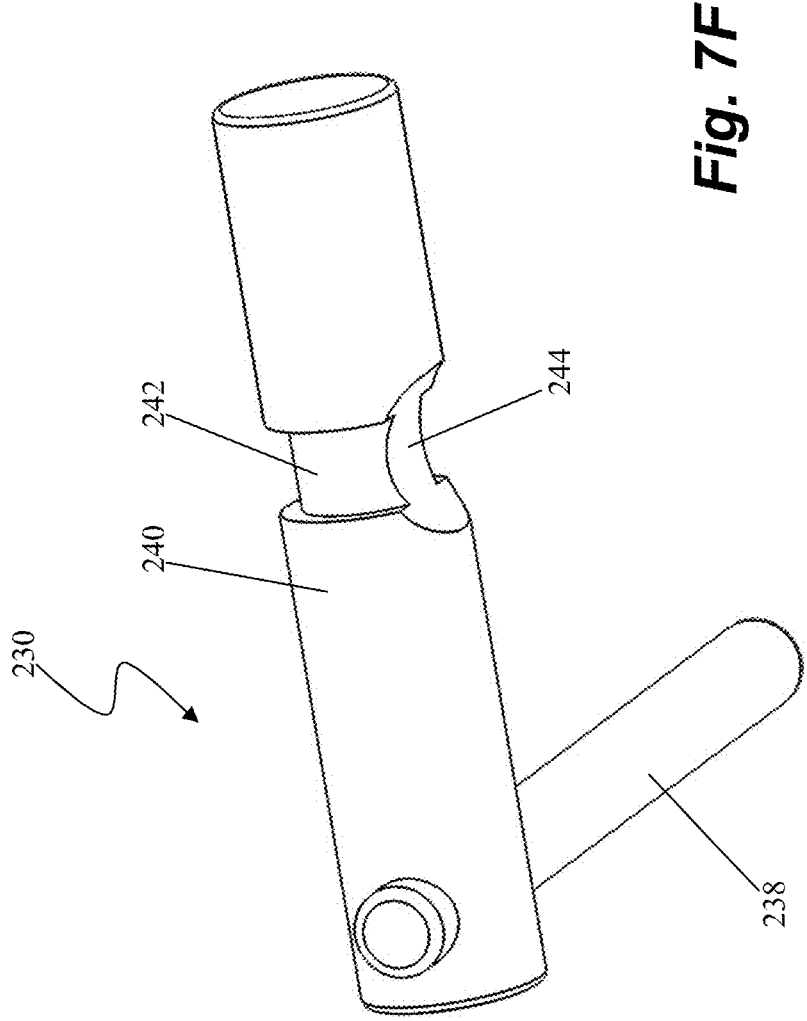

FIGS. 6A-6B depict device 100 with an insertion device 200 used to insert and expand device 100 within the disc space according to an embodiment. As will be described in more detail below, insertion device 200 generally includes a stabilizing component 204 and an expansion component 202. Expansion component 202 includes a knob 209 configured to be rotated to secure the expansion component 202 to intervertebral device 100 and a dial 208 configured to be rotated to expand intervertebral device 100, as discussed in more detail below. Stabilizing component 204 includes a handle 206 configured to be rotated to secure the component to device 100. FIGS. 7A-7E depict further detail regarding the components of insertion device 200.

Expansion component 202 includes a body 224, a shaft 222 extending from the body 224, a flange 226 at the distal end of shaft 222 and a distal threaded tip 228. Shaft 222 and body 224 include internal lumens that enable passage of shaft body 214 of stabilizing component 204 to pass through expansion component 202. Distal tip 228 is sized to be rotatingly received by posterior or proximal threaded opening 126 of device. Flange 226 is wider than shaft 222 and threaded tip 228 to prevent expansion component 204 from being over-inserted when attached to expandable device 100. Knob 209 and dial 208 are selectively attachable to expansion component 202 via, for example, a rotational coupling with knob 209 and with a screw 220 for dial 208. Dial 208 can also include a threaded portion 221 configured to interface with a proximal threaded portion 212 of shaft 210. A lock 230 can be selectively insert into a lock aperture 232 through body 224 of expansion component 202 to lock rotation of stabilizing component 204 with respect to expansion component 202, as will be discussed in more detail below. Lock 230 can be selectively held in place with screw 234.

Stabilizing component 204 includes a shaft 210 extending from handle 206. Shaft 210 includes a proximal threaded portion 212 configured to interface with dial 208, a shaft body 214 configured to be extended through the expansion component 202, an implant extension 216 configured to extend through the implantable device 100 during implantation, and a threaded tip 218. Shaft 210 further includes a lock slot 236 configured to interface with lock 230.

Lock 230 includes a handle 238 and a lock body 240. Lock body 240 is configured to be inserted through lock aperture 232 in body 224 of stabilizing component 202. Lock body 240 further includes a recessed portion 242 having a reduced diameter that interfaces with the lock slot 236 in shaft body 214 of shaft 210. Recessed portion 242 of lock body 240 further includes a cutout 244 that allows for limited rotation of shaft body 214 when lock 230 is engaged with shaft 210.

Figure 8A:
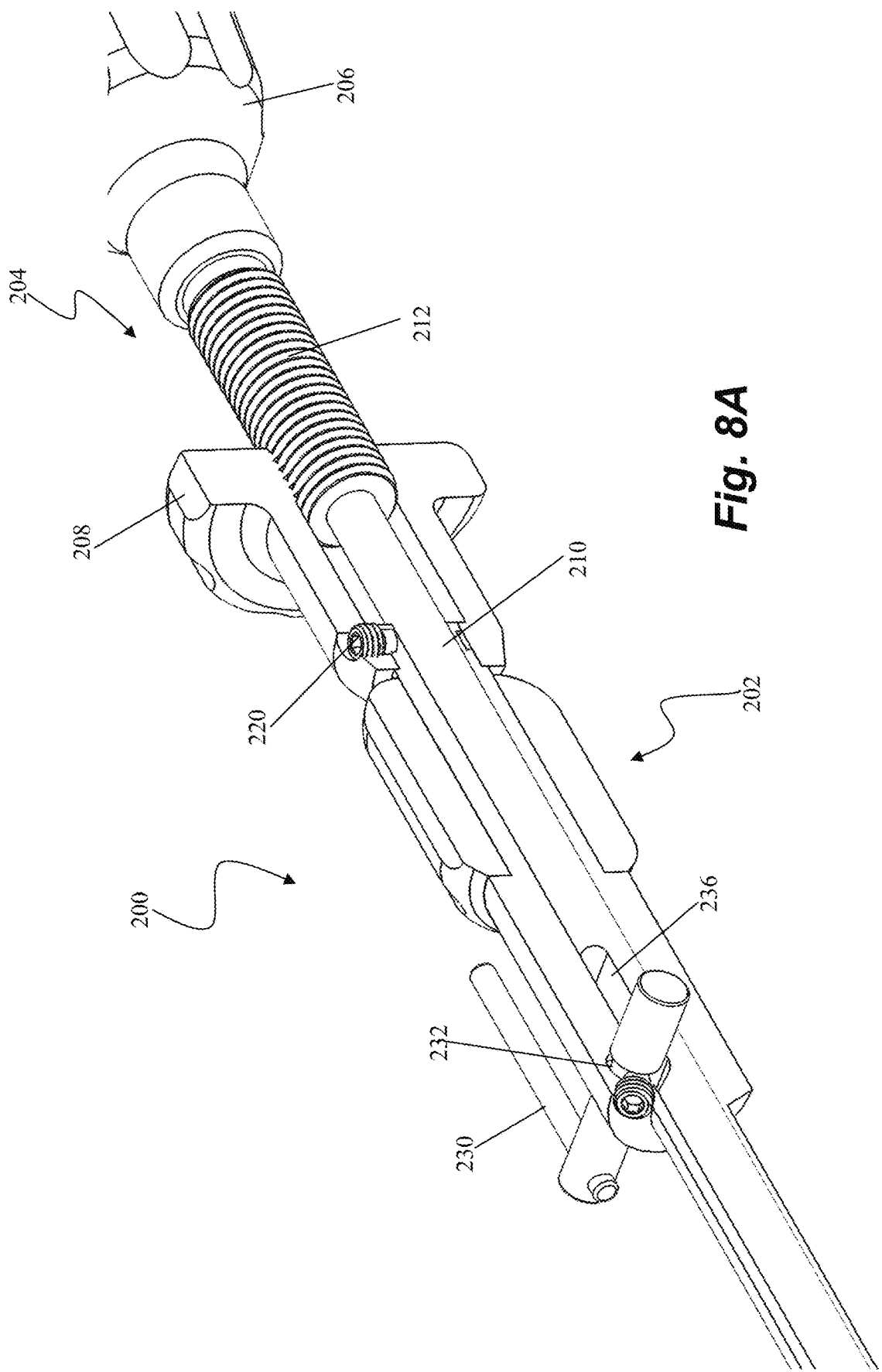

FIGS. 8A-8C further depict the interrelation of the components of inserter 200. Dial 208 is threaded onto proximal threaded portion 212 of stabilizing component 204. Shaft 210 of stabilizing component is inserted through expansion component 202 with implant extension 216 and threaded tip 218 extending distally from expansion component 202. Proximal end of expansion component 202 is secured to dial 208 with screw 220. Lock 230 can be selectively inserted into aperture 232 and through lock slot 236 in shaft 210.

FIGS. 9A-9I depict further details regarding the interaction between inserter 200 and expandable device 100. First, the distal tip 228 of the expansion component 202 is engaged with the posterior threaded opening 126 of implantable device 100 and the knob 209 is rotated to secure the tip 228 to the opening 126. If not already done so prior to attaching expansion component 202, stabilizing component 204 is inserted through stabilizing component 202 to the distal side of the expandable device 100. The implant extension 216 can be extended through the body of the implant 100 to engage the threaded tip 218 of the stabilizing component 204 to interface with the distal threaded opening 124 of the implant. Handle 206 can be rotated to secure the tip 218 to the opening 124. Lock 230 can now be inserted through slot 232 in expansion component and across slot 236 in shaft 214 of stabilizing component.

The dial 208 of the expansion component 202 can now be rotated to expand the implant 100 within the disc space. Dial 208 is rotated while the user holds the knob 209 such that the dial rotates relative to knob 209. Lock 230 prevents shaft 214 from rotating such that stabilizing component 204 maintains device 100 in a stable position. Dial 208 therefore rotates shaft 222 and distal tip 228 about shaft 214 of stabilizing component 204. This rotation pushes on the proximal or anterior end of device 100 while the distal or posterior end of the device is maintained stable, causing the distance between the anterior and posterior ends of the device to shorten and the device 100 to expand laterally outwardly. As described, above, device expands from the collapsed configuration shown in, e.g., FIGS. 1A, 5A and 6A, to the expanded configuration shown in, e.g., FIGS. 2A, 5B and 6B to cover a wider footprint in the disc space.

Implant is therefore able to provide more robust and stable support in the disc space that is laterally wider than the access opening through which the implant is implanted.

Figure 9A:
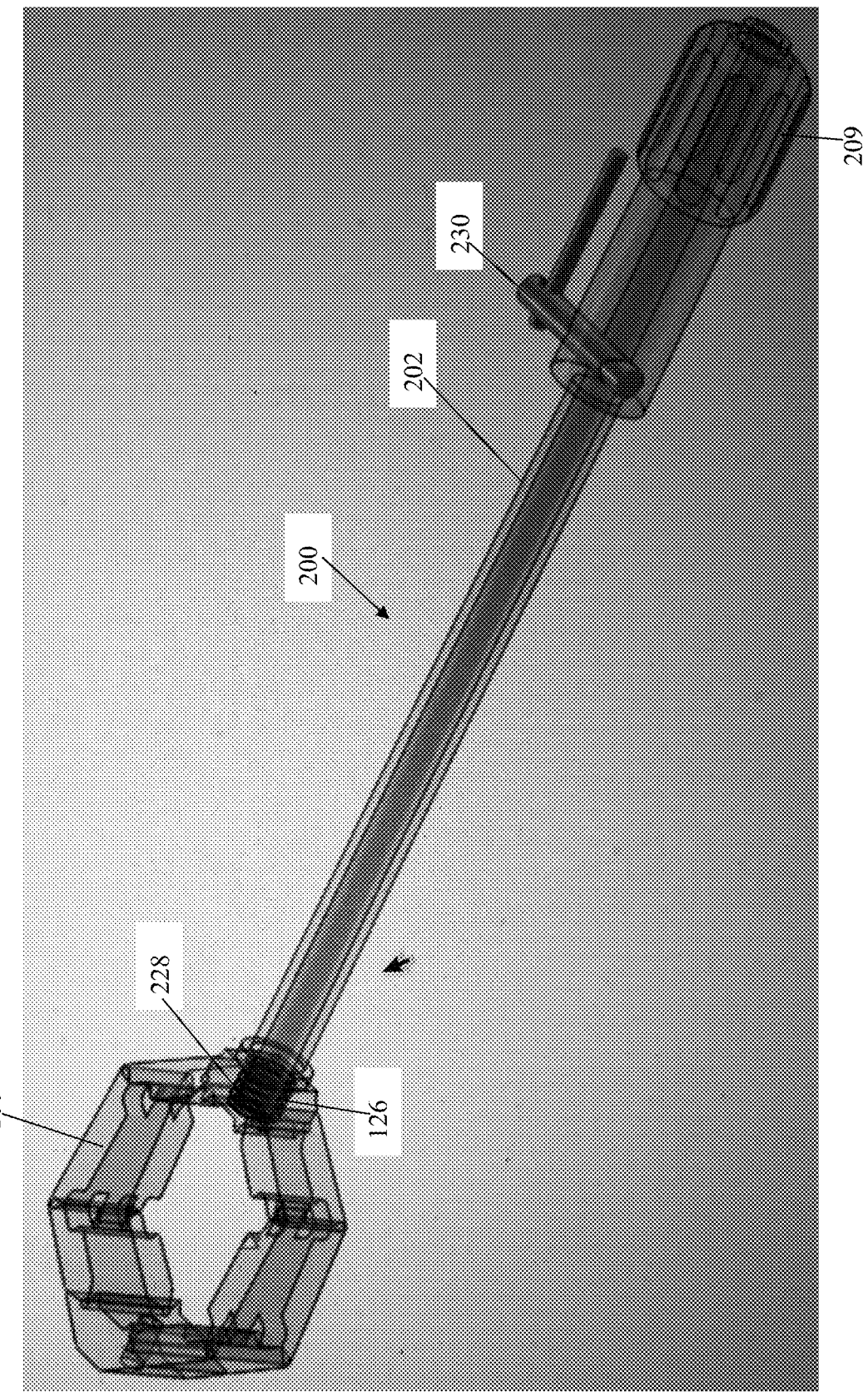
FIGS. 9A-9I depict portions of an insertion device and an expandable intervertebral body fusion device according to an embodiment While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.
Figure 9B:
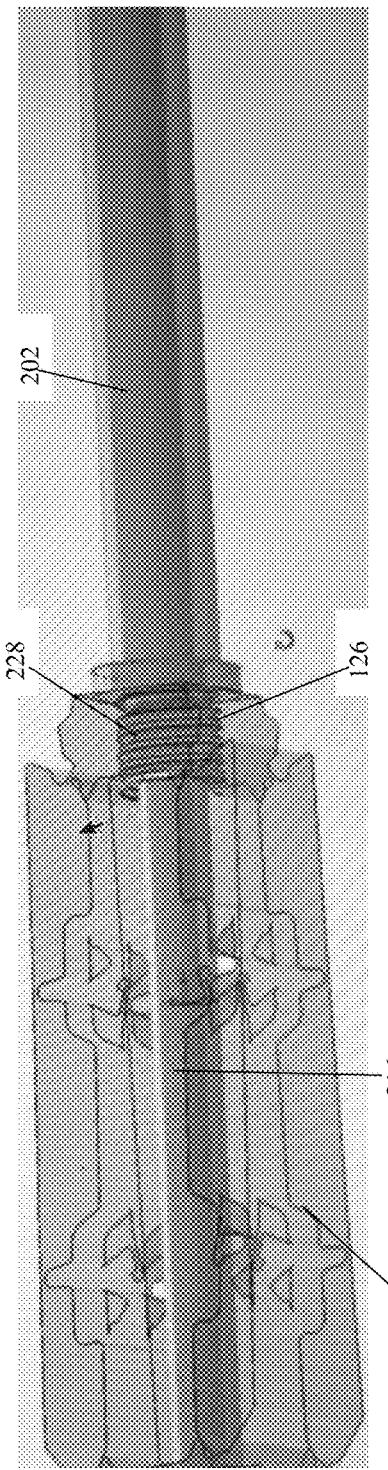
Figure 9C:
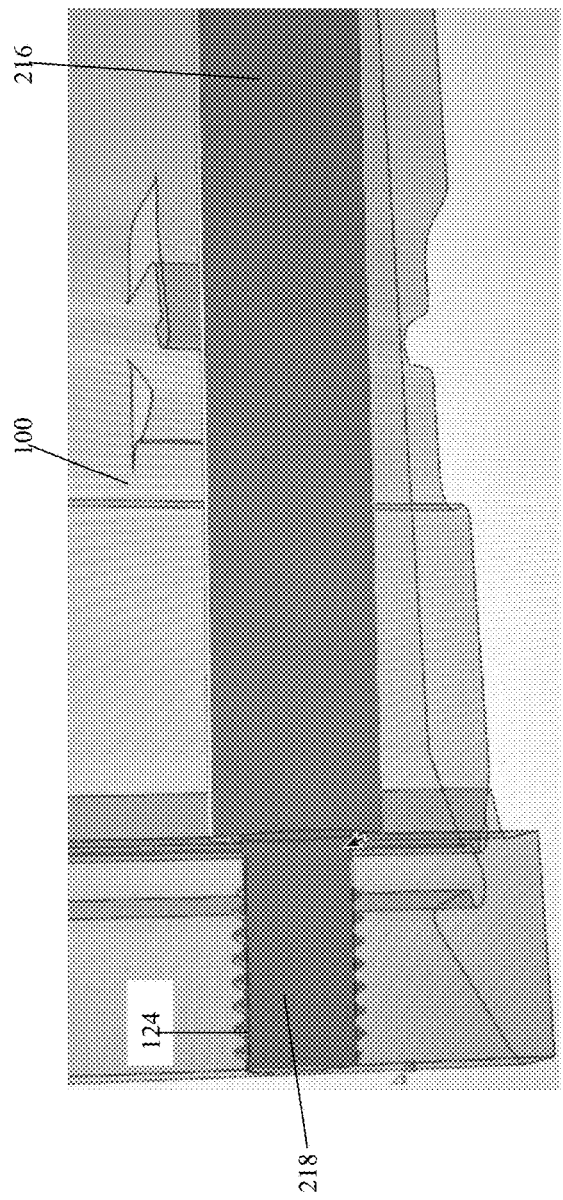
Figure 9D:
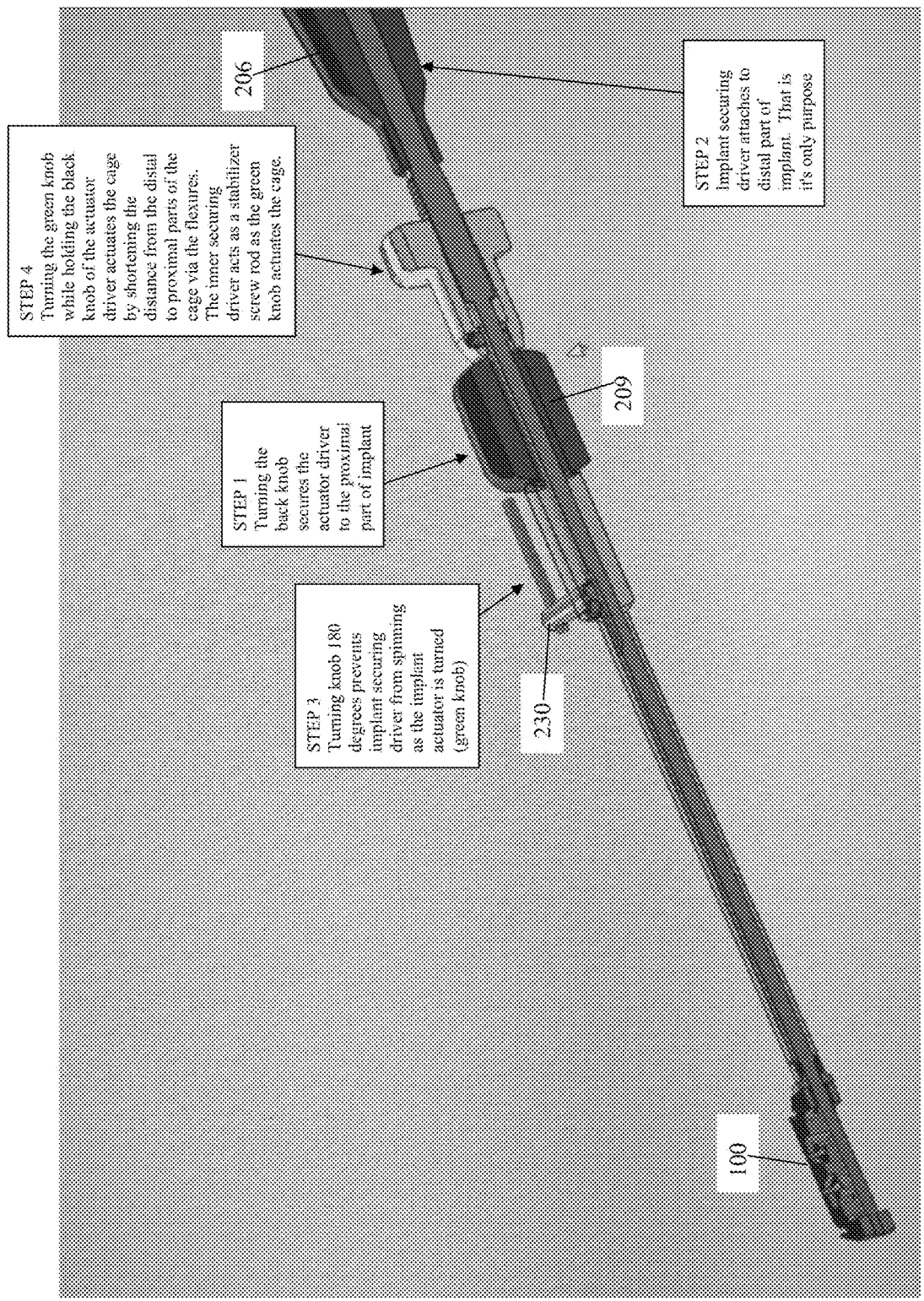
Figure 9F:
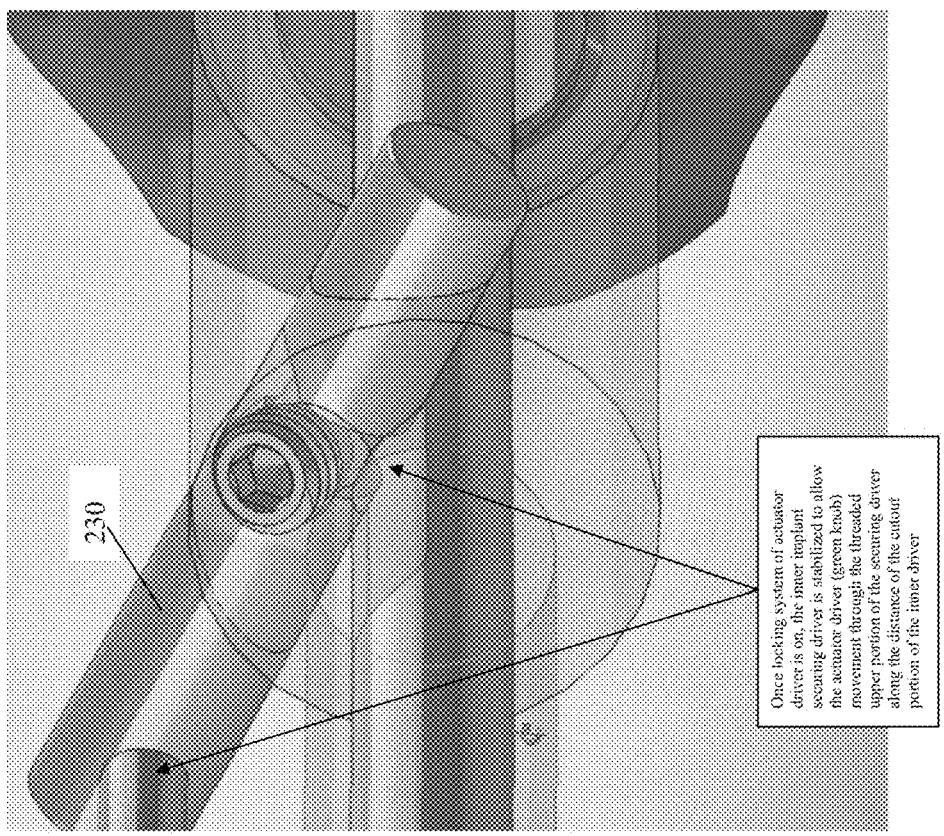
Figure 9E:
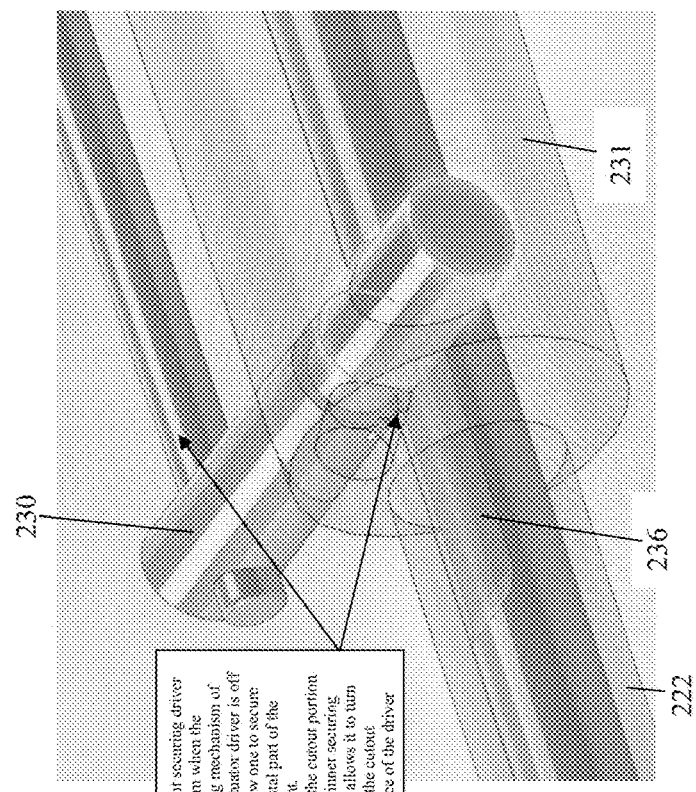
Figure 9G:
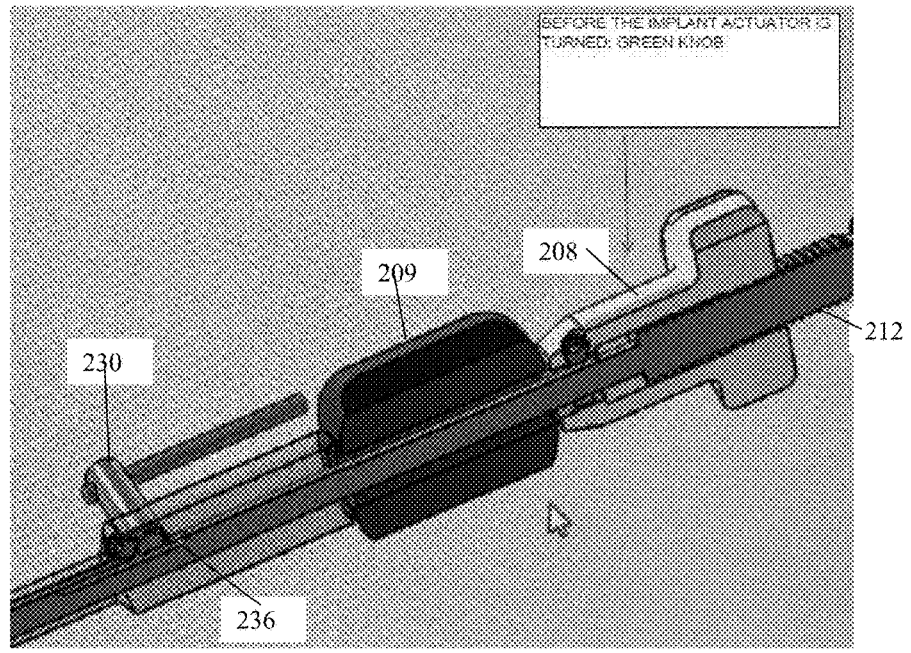
Figure 9H:
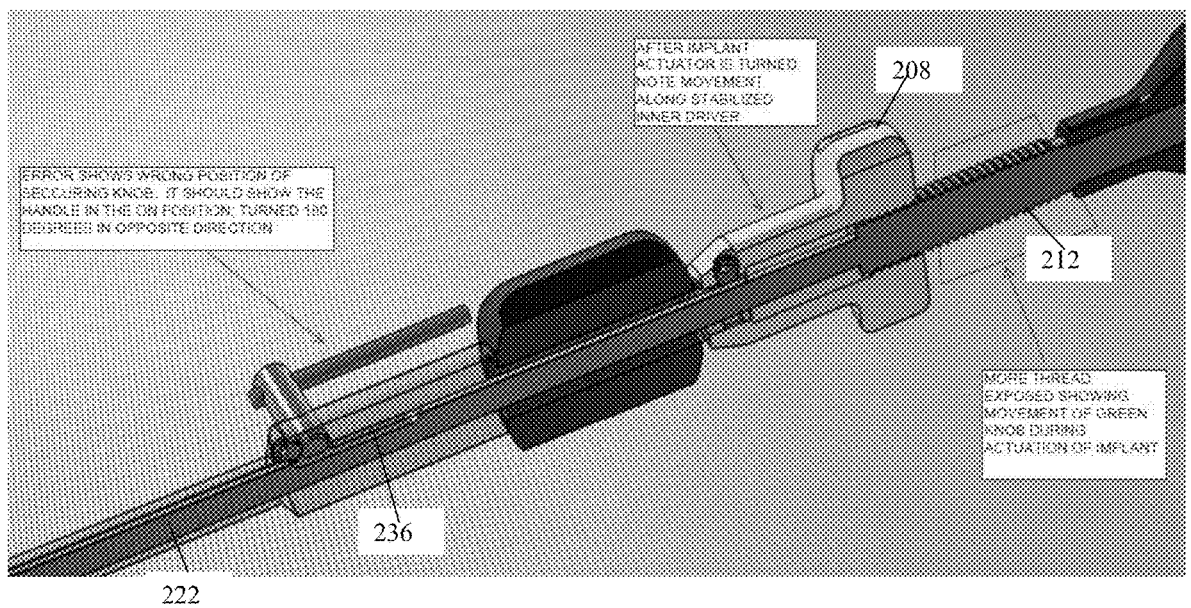

As can be seen in FIGS. 9E-9H, the slot 236 in shaft 210 of stabilizing component 204 can also serve to limit an amount that expansion component 202 can be rotated to expand device 100. Referring to FIGS. 9E and 9G, initially the lock 230 is positioned in at a proximal end of slot 236. As the dial 208 is rotated to rotate the shaft 222 to expand the device 100, the dial 208 travels linearly along the threaded portion 212 of the stabilizing component and the lock 230, which is inserted through a locking tube 231 of expansion component that enables shaft 222 to be rotated, is advanced linearly along slot 236. In the fully expanded position, as shown in FIG. 9H, the lock 230 abuts a distal end of the slot 236 such that further rotation of dial 208 with not cause any further linear advancement of shaft 222. The length of the slot 236 can be predetermined based on a desired or actual maximum expansion of the implanted device 100.

Figure 9I:
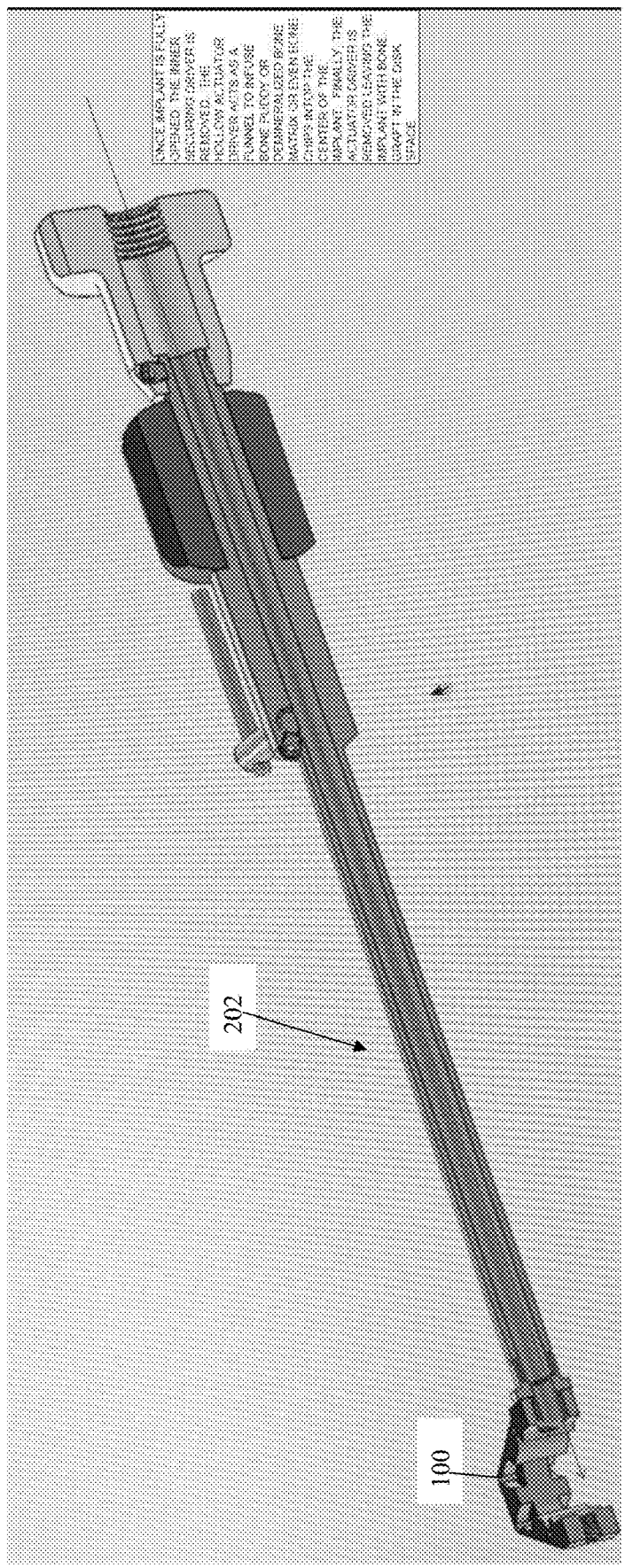

Referring to FIG. 9I, the stabilizing component 204 can be removed by rotating handle 206 to disengage the threaded tip 218 from the device and withdrawing the shaft 210 from the expansion component 202. The hollow expansion component 202 can then serve as a funnel to infuse one or more of, for example, bone puddy, demineralized bone matrix, and bone chips into the now empty opening in the device 100 to aid the fusion process. Finally, the expansion component 202 can be disengaged from the implant 100 and removed, leaving the implant in the disc space with, e.g., bone graft in the interior of the device 100.

The typical height opening after a discectomy available to insert the implant can be from 4-14 mm depending on how collapsed the disc space is. One would need disc space distractors either a mechanical device or a lollipop sizer to expand the disc space. The typical width of the surgical path into the disc space after retracting the nerve root could be 10-12 mm. Through a transforaminal interbody approach (TLIF: transforaminal interbody fusion) where you remove the superior and inferior facet you may be able to get an additional 1-2 mm more of working room.

In another embodiment, device can be inserted into the disc space and expanded vertically to expand the disc space, with the flexures locking the device at the expanded height and maintaining the expanded disc space.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An expandable intervertebral body fusion device, comprising:
   a unitary monolithic body, the body having a plurality of body segments connected to each other with flexure members and an opening defined between the plurality of body segments, including—
   an anterior body segment;
   a posterior body segment;
   one or more mediolateral body segments extending between the anterior body segment and the posterior body segment along both a lateral side and a medial side of the anterior body segment and the posterior body segment;
   a threaded opening formed in both the anterior body segment and the posterior body segment, and wherein the threaded opening in the posterior body segment has a larger diameter than the threaded opening in the anterior body segment; and
   wherein the body is configured to be mediolaterally expanded from a compressed configuration to an expanded configuration by interaction of an expansion tool with the threaded openings causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration with a maximum anterior to posterior width of the expanded configuration defined between the anterior body segment and the posterior body segment and a maximum medial to lateral width of the expanded configuration defined between two mediolateral body segments.

2. The expandable intervertebral body fusion device of claim 1, wherein the threaded opening on the posterior body segment is configured to interface with an expansion element configured to be rotated to expand the body to the expanded configuration and the threaded opening on the anterior body segment is configured to interface with a stabilizing element configured to stabilize the body when the body is expanded.

3. The expandable intervertebral body fusion device of claim 1, wherein the threaded opening formed in the anterior body segment is aligned coaxially with the threaded opening formed in the posterior body segment.

4. The expandable intervertebral body fusion device of claim 1, the body further comprises one or more locking flexures configured to lock the body in the expanded configuration.

5. The expandable intervertebral body fusion device of claim 4, wherein there is at least one locking flexure extending from at least one mediolateral body segment on each of the lateral side and the medial side, and wherein each locking flexure is configured to interlock with an adjacent body segment.

6. The expandable intervertebral body fusion device of claim 4, wherein each locking flexure comprises a flexible elongate body with a locking tip and is configured to interlock with a locking projection extending outwardly from an adjacent body segment.

7. The expandable intervertebral body fusion device of claim 1, wherein there are three mediolateral body segments along each of the lateral side and the medial side.

8. The expandable intervertebral body fusion device of claim 1, wherein in the expanded configuration the body has a generally polygonal shape.

9. The expandable intervertebral body fusion device of claim 1, wherein in the expanded configuration the mediolateral footprint is approximately doubled in width from the compressed configuration.

10. A transversely expandable intervertebral body fusion device for a disc space between adjacent vertebra of a spine of a human patient, the device comprising:
   a unitary monolithic body configured in size and shape to be implantable in the disc space, the body having at least four body segments each connected to adjacent body segments by one or more flexure members, the body segments surrounding and collectively defining an opening within a transverse plane bisecting the body, the body segments including—
      an anterior body segment;
      a posterior body segment; and
      at least one mediolateral body segment extending between the anterior body segment and the posterior body segment along each of a lateral side and a medial side of the body; and
   a threaded opening formed in both of the anterior body segment and the posterior body segment;
   wherein the body is configured to be mediolaterally expanded from a transversely compressed configuration to a transversely expanded configuration by interaction of an expansion tool with the threaded openings causing the at least one mediolateral body segments on each side to generally move transversely away from each other, thereby expanding the opening of the body and forming a generally continuous outermost footprint defined by an outer edge of the anterior body segment, the posterior body segment and two of the mediolateral body segments that presents a mediolateral footprint in the expanded configuration that is greater than in the compressed configuration, and
   wherein the body further comprises at least one locking flexure extending from at least one mediolateral body segment on each of the lateral side and the medial side, wherein each locking flexure comprises a flexible elongate body with a locking tip and is configured to interlock with a locking projection extending outwardly from an adjacent body segment.

11. The expandable intervertebral body fusion device of claim 10, wherein the threaded opening on the posterior body segment is configured to interface with an expansion element configured to be rotated to expand the body to the expanded configuration and the threaded opening on the anterior body segment is configured to interface with a stabilizing element configured to stabilize the body when the body is expanded.

12. The expandable intervertebral body fusion device of claim 10, wherein the threaded opening formed in the anterior body segment is aligned coaxially with the threaded opening formed in the posterior body segment.

13. The expandable intervertebral body fusion device of claim 10, wherein the threaded opening formed in the anterior body segment has a smaller diameter than the threaded opening formed in the posterior body segment.

14. The expandable intervertebral body fusion device of claim 10, wherein there are three mediolateral body segments along each of the lateral side and the medial side.

15. The expandable intervertebral body fusion device of claim 10, wherein in the expanded configuration the body has a generally polygonal shape.

16. The expandable intervertebral body fusion device of claim 10, wherein in the expanded configuration the mediolateral footprint is approximately doubled in width from the compressed configuration.

* * * * *